(12) United States Patent
Groux et al.

(10) Patent No.: US 9,255,295 B2
(45) Date of Patent: Feb. 9, 2016

(54) METHOD FOR EVALUATING THE SENSITIZING POTENTIAL OF A TEST COMPOUND

(75) Inventors: Hervé Groux, Le Rouret (FR); Françoise Cottrez, Le Rouret (FR)

(73) Assignee: IMMUNOSEARCH, Le Plan de Grasse (FR)

( * ) Notice: Subject to any disclaimer, the term of this patent is extended or adjusted under 35 U.S.C. 154(b) by 8 days.

(21) Appl. No.: 13/582,930

(22) PCT Filed: Mar. 7, 2011

(86) PCT No.: PCT/FR2011/000122
§ 371 (c)(1),
(2), (4) Date: Oct. 4, 2012

(87) PCT Pub. No.: WO2011/107679
PCT Pub. Date: Sep. 9, 2011

(65) Prior Publication Data
US 2013/0005602 A1    Jan. 3, 2013

(30) Foreign Application Priority Data
Mar. 5, 2010    (FR) ........................... 10 51636

(51) Int. Cl.
*C12Q 1/68*    (2006.01)
(52) U.S. Cl.
CPC ........ *C12Q 1/6883* (2013.01); *C12Q 2600/136* (2013.01); *C12Q 2600/158* (2013.01)
(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 5,854,033 | A | 12/1998 | Lizardi |
| 6,103,482 | A | 8/2000 | Schmidt et al. |
| 2009/0035294 | A1* | 2/2009 | Mahe et al. ............... 424/94.63 |

FOREIGN PATENT DOCUMENTS

| | | |
|---|---|---|
| EP | 0857971 A1 | 8/1998 |
| WO | WO 02/070729 A2 | 9/2002 |
| WO | WO 2007/090575 A1 | 8/2007 |

OTHER PUBLICATIONS

Frederick et al (American Journal of Pathology, vol. 156, No. 6, Jun. 2000, e.g., entire document, see title and abstract).*
Hayes et al (Antioxidants & Redox Signaling Dec. 1, 2010, 13.11 1713 No. 36 pp. 1-46).*
Netzlaff et al (European Journal of Pharmaceutics and Biopharmaceutics 2005: vol. 60 pp. 167-178).*
Borlon et al (Toxicology, 2007, vol. 241, pp. 157-166.*
Ponec in "In vitro cultured human skin cells as alternatives to animals for skin irritancy screening" (International Journal of Cosmetic Science 1992 vol. 14, pp. 245-264).*
Barany, "Genetic disease detection and DNA amplification using cloned thermostable ligase," Proceedings of the National Academy of Sciences USA, vol. 88, pp. 189-193, Jan. 1991.
Bellon et al., "Differential gene expression in drug hypersensitivity reactions: induction of alarmins in severe bullous diseases," Clinical and Laboratory Investigations, British Journal of Dermatology, vol. 162, 2010, pp. 1014-1022, XP055007187.
Borlon et al., "The usefulness of toxicogenomics for predicting acute skin irritation on in vitro reconstructed human epidermis," Toxicology, vol. 241, 2007, pp. 157-166, XP022310517.
Fletcher et al., "Gene expression analysis of EpiDerm™ following exposure to SLS using cDNA microarrays," Toxicology in Vitro, vol. 15, 2001, pp. 393-398, XP007915270.
Friedmann, "The relationships between exposure dose and response in induction and elicitation of contact hypersensitivity in humans," British Journal of Dermatology, vol. 157, 2007, pp. 1093-1102, XP002636187.
Guatelli et al., "Isothermal, in vitro amplification of nucleic acids by a multienzyme reaction modeled after retroviral replication," Proceedings of the National Academy of Sciences USA, vol. 87, Mar. 1990, pp. 1874-1878.
International Search Report dated Octber 6, 2011 for International Application No. PCT/FR2011/000122 (PCT/ISA/210).
Kwoh et al., "Transcription-based amplification system and detection of amplified human immunodeficiency virus type 1 with a bead-based sandwich hybridization format," Proceedings of the National Academy of Science USA, vol. 86, Feb. 1989, pp. 1173-1177.
Mitsui et al., "Kinetic profiles of sequential gene expressions for chemokines in mice with contact hypersensitivity," Immunology Letters, vol. 68, 2003, pp. 191-197, XP002604478.
Niwa et al., "Evaluation of the Skin Irritation Using a DNA Microarray on a Reconstructed Human Epidermal Model," Biological and Pharmaceutical Bulletin, vol. 32, No. 2, 2009, pp. 203-208, XP002603918.
Sec et al., "Expression of Neutrophil Gelatinase-Associated Lipocalin in Skin Epidermis," Journal of Investigative Dermatology, vol. 126, 2006, pp. 510-512, XP002559163.

* cited by examiner

*Primary Examiner* — Catherine S Hibbert
(74) *Attorney, Agent, or Firm* — Birch, Stewart, Kolasch & Birch, LLP

(57) ABSTRACT

The invention relates to a method for evaluating the sensitizing potential of a test compound, and to a kit for implementing said method.

14 Claims, No Drawings

SEQUENCE LISTING

<160> NUMBER OF SEQ ID NOS: 82

<210> SEQ ID NO 1

```
<211> LENGTH: 24
<212> TYPE: DNA
<213> ORGANISM: artificial
<220> FEATURE:
<223> OTHER INFORMATION: Forward primer BRAK

<400> SEQUENCE: 1
aagtacccgc actgcgagga gaag                                          24

<210> SEQ ID NO 2
<211> LENGTH: 24
<212> TYPE: DNA
<213> ORGANISM: artificial
<220> FEATURE:
<223> OTHER INFORMATION: Reverse primer BRAK

<400> SEQUENCE: 2
ttggtgctct gcagcttggg gtgc                                          24

<210> SEQ ID NO 3
<211> LENGTH: 24
<212> TYPE: DNA
<213> ORGANISM: artificial
<220> FEATURE:
<223> OTHER INFORMATION: Forward primer CTSS

<400> SEQUENCE: 3
tcatacgatc tgggcatgaa ccac                                          24

<210> SEQ ID NO 4
<211> LENGTH: 24
<212> TYPE: DNA
<213> ORGANISM: artificial
<220> FEATURE:
<223> OTHER INFORMATION: Reverse primer CTSS

<400> SEQUENCE: 4
tgggaactct cagggaactc atca                                          24

<210> SEQ ID NO 5
<211> LENGTH: 24
<212> TYPE: DNA
<213> ORGANISM: artificial
<220> FEATURE:
<223> OTHER INFORMATION: Forward primer DAPK2

<400> SEQUENCE: 5
tttccttcag catcgtgtcc ctgt                                          24

<210> SEQ ID NO 6
<211> LENGTH: 24
<212> TYPE: DNA
<213> ORGANISM: artificial
<220> FEATURE:
<223> OTHER INFORMATION: Reverse primer DAPK2

<400> SEQUENCE: 6
tgtcactctc acagttcctc aggt                                          24

<210> SEQ ID NO 7
<211> LENGTH: 24
<212> TYPE: DNA
<213> ORGANISM: artificial
<220> FEATURE:
<223> OTHER INFORMATION: Forward primer FABP4

<400> SEQUENCE: 7
```

```
actgggccag gaatttgacg aagt                                              24

<210> SEQ ID NO 8
<211> LENGTH: 24
<212> TYPE: DNA
<213> ORGANISM: artificial
<220> FEATURE:
<223> OTHER INFORMATION: Reverse primer FABP4

<400> SEQUENCE: 8
tttctgcaca tgtaccagga cacc                                              24

<210> SEQ ID NO 9
<211> LENGTH: 23
<212> TYPE: DNA
<213> ORGANISM: artificial
<220> FEATURE:
<223> OTHER INFORMATION: Forward primer HSP27

<400> SEQUENCE: 9
tgcttcacgc ggaaatacac gct                                               23

<210> SEQ ID NO 10
<211> LENGTH: 24
<212> TYPE: DNA
<213> ORGANISM: artificial
<220> FEATURE:
<223> OTHER INFORMATION: Reverse primer HSP27

<400> SEQUENCE: 10
ctgggatggt gatctcgttg gact                                              24

<210> SEQ ID NO 11
<211> LENGTH: 24
<212> TYPE: DNA
<213> ORGANISM: artificial
<220> FEATURE:
<223> OTHER INFORMATION: Forward primer IL18

<400> SEQUENCE: 11
tcattgacca aggaaatcgg cctc                                              24

<210> SEQ ID NO 12
<211> LENGTH: 23
<212> TYPE: DNA
<213> ORGANISM: artificial
<220> FEATURE:
<223> OTHER INFORMATION: Reverse primer IL18

<400> SEQUENCE: 12
agccatacct ctaggctggc tat                                               23

<210> SEQ ID NO 13
<211> LENGTH: 23
<212> TYPE: DNA
<213> ORGANISM: artificial
<220> FEATURE:
<223> OTHER INFORMATION: Forward primer IL1R2

<400> SEQUENCE: 13
gccagccttg caggaggact ctg                                               23

<210> SEQ ID NO 14
<211> LENGTH: 24
<212> TYPE: DNA
```

```
<213> ORGANISM: artificial
<220> FEATURE:
<223> OTHER INFORMATION: Reverse primer IL1R2

<400> SEQUENCE: 14
ttgcgggtat gagatgaacg gcag                                          24

<210> SEQ ID NO 15
<211> LENGTH: 24
<212> TYPE: DNA
<213> ORGANISM: artificial
<220> FEATURE:
<223> OTHER INFORMATION: Forward primer TPSAB1

<400> SEQUENCE: 15
acggcccata ctggatgcac ttct                                          24

<210> SEQ ID NO 16
<211> LENGTH: 23
<212> TYPE: DNA
<213> ORGANISM: artificial
<220> FEATURE:
<223> OTHER INFORMATION: Reverse primer TPSAB1

<400> SEQUENCE: 16
cagcagctgg tcctggtagt aga                                           23

<210> SEQ ID NO 17
<211> LENGTH: 22
<212> TYPE: DNA
<213> ORGANISM: artificial
<220> FEATURE:
<223> OTHER INFORMATION: Forward primer CXCR1

<400> SEQUENCE: 17
tatgaatctg tccctgccct tc                                            22

<210> SEQ ID NO 18
<211> LENGTH: 24
<212> TYPE: DNA
<213> ORGANISM: artificial
<220> FEATURE:
<223> OTHER INFORMATION: Reverse primer CXCR1

<400> SEQUENCE: 18
acctcatagc aaactggact ggaa                                          24

<210> SEQ ID NO 19
<211> LENGTH: 24
<212> TYPE: DNA
<213> ORGANISM: artificial
<220> FEATURE:
<223> OTHER INFORMATION: Forward primer DEFB1

<400> SEQUENCE: 19
ttcctgaaat cctgggtgtt gcct                                          24

<210> SEQ ID NO 20
<211> LENGTH: 24
<212> TYPE: DNA
<213> ORGANISM: artificial
<220> FEATURE:
<223> OTHER INFORMATION: Reverse primer DEFB1

<400> SEQUENCE: 20
aggcctgtga gaaagttacc acct                                          24
```

```
<210> SEQ ID NO 21
<211> LENGTH: 24
<212> TYPE: DNA
<213> ORGANISM: artificial
<220> FEATURE:
<223> OTHER INFORMATION: Forward primer DHFR

<400> SEQUENCE: 21
ctcattttct ttccagaagt ctag                                          24

<210> SEQ ID NO 22
<211> LENGTH: 24
<212> TYPE: DNA
<213> ORGANISM: artificial
<220> FEATURE:
<223> OTHER INFORMATION: Reverse primer DHFR

<400> SEQUENCE: 22
tgccaccaac tatccagacc atgt                                          24

<210> SEQ ID NO 23
<211> LENGTH: 24
<212> TYPE: DNA
<213> ORGANISM: artificial
<220> FEATURE:
<223> OTHER INFORMATION: Forward primer EHF

<400> SEQUENCE: 23
ttggctctct catgtccttg gctt                                          24

<210> SEQ ID NO 24
<211> LENGTH: 24
<212> TYPE: DNA
<213> ORGANISM: artificial
<220> FEATURE:
<223> OTHER INFORMATION: Reverse primer EHF

<400> SEQUENCE: 24
aggtatgaca ctgtggtagg tgct                                          24

<210> SEQ ID NO 25
<211> LENGTH: 24
<212> TYPE: DNA
<213> ORGANISM: artificial
<220> FEATURE:
<223> OTHER INFORMATION: Forward primer IVL

<400> SEQUENCE: 25
tgcccacaaa gggagaagta ttgc                                          24

<210> SEQ ID NO 26
<211> LENGTH: 24
<212> TYPE: DNA
<213> ORGANISM: artificial
<220> FEATURE:
<223> OTHER INFORMATION: Reverse primer IVL

<400> SEQUENCE: 26
tctggacact gcgggtggtt attt                                          24

<210> SEQ ID NO 27
<211> LENGTH: 24
<212> TYPE: DNA
<213> ORGANISM: artificial
<220> FEATURE:
```

-continued

<223> OTHER INFORMATION: Forward primer KRT4

<400> SEQUENCE: 27
tcacatatgt cccttcccag tcca                                              24

<210> SEQ ID NO 28
<211> LENGTH: 24
<212> TYPE: DNA
<213> ORGANISM: artificial
<220> FEATURE:
<223> OTHER INFORMATION: Reverse primer KRT4

<400> SEQUENCE: 28
tgccgggtgt tggagaagta gttt                                              24

<210> SEQ ID NO 29
<211> LENGTH: 24
<212> TYPE: DNA
<213> ORGANISM: artificial
<220> FEATURE:
<223> OTHER INFORMATION: Forward primer MELANA

<400> SEQUENCE: 29
tcttactgct catcggctgt tggt                                              24

<210> SEQ ID NO 30
<211> LENGTH: 24
<212> TYPE: DNA
<213> ORGANISM: artificial
<220> FEATURE:
<223> OTHER INFORMATION: Reverse primer MELANA

<400> SEQUENCE: 30
tgaagagaca ctttgctgtc ccga                                              24

<210> SEQ ID NO 31
<211> LENGTH: 24
<212> TYPE: DNA
<213> ORGANISM: artificial
<220> FEATURE:
<223> OTHER INFORMATION: Forward primer NGAL

<400> SEQUENCE: 31
gtgagcacca actacaacca gcat                                              24

<210> SEQ ID NO 32
<211> LENGTH: 24
<212> TYPE: DNA
<213> ORGANISM: artificial
<220> FEATURE:
<223> OTHER INFORMATION: Reverse primer NGAL

<400> SEQUENCE: 32
agttccgaag tcagctcctt ggtt                                              24

<210> SEQ ID NO 33
<211> LENGTH: 24
<212> TYPE: DNA
<213> ORGANISM: artificial
<220> FEATURE:
<223> OTHER INFORMATION: Forward primer PDZK11P1

<400> SEQUENCE: 33
caatcgcctt tgcagtcaac cact                                              24

<210> SEQ ID NO 34
<211> LENGTH: 24
<212> TYPE: DNA
<213> ORGANISM: artificial
<220> FEATURE:
<223> OTHER INFORMATION: Reverse primer PDZK11P1

<400> SEQUENCE: 34
accaggactc catctgcctt gttt                                          24

<210> SEQ ID NO 35
<211> LENGTH: 24
<212> TYPE: DNA
<213> ORGANISM: artificial
<220> FEATURE:
<223> OTHER INFORMATION: Forward primer PI3

<400> SEQUENCE: 35
tcttgatcgt ggtggtgttc ctca                                          24

<210> SEQ ID NO 36
<211> LENGTH: 24
<212> TYPE: DNA
<213> ORGANISM: artificial
<220> FEATURE:
<223> OTHER INFORMATION: Reverse primer PI3

<400> SEQUENCE: 36
gactggctct tgcgctttga cttt                                          24

<210> SEQ ID NO 37
<211> LENGTH: 24
<212> TYPE: DNA
<213> ORGANISM: artificial
<220> FEATURE:
<223> OTHER INFORMATION: Forward primer PSME2

<400> SEQUENCE: 37
tccctcaatg tggctgactt gact                                          24

<210> SEQ ID NO 38
<211> LENGTH: 24
<212> TYPE: DNA
<213> ORGANISM: artificial
<220> FEATURE:
<223> OTHER INFORMATION: Reverse primer PSME2

<400> SEQUENCE: 38
tctcattccc agggagaaat ccac                                          24

<210> SEQ ID NO 39
<211> LENGTH: 24
<212> TYPE: DNA
<213> ORGANISM: artificial
<220> FEATURE:
<223> OTHER INFORMATION: Forward primer SERPINB3

<400> SEQUENCE: 39
actcctgggt ggaaagtcaa acga                                          24

<210> SEQ ID NO 40
<211> LENGTH: 24
<212> TYPE: DNA
<213> ORGANISM: artificial
<220> FEATURE:
<223> OTHER INFORMATION: Reverse primer SERPINB3

```
<400> SEQUENCE: 40
actcctgggt ggaaagtcaa acga                                          24

<210> SEQ ID NO 41
<211> LENGTH: 24
<212> TYPE: DNA
<213> ORGANISM: artificial
<220> FEATURE:
<223> OTHER INFORMATION: Forward primer AKR1B10

<400> SEQUENCE: 41
aagatgataa aggtaatgcc atcg                                          24

<210> SEQ ID NO 42
<211> LENGTH: 24
<212> TYPE: DNA
<213> ORGANISM: artificial
<220> FEATURE:
<223> OTHER INFORMATION: Reverse primer AKR1B10

<400> SEQUENCE: 42
agcttctcga tctggaagtg gctg                                          24

<210> SEQ ID NO 43
<211> LENGTH: 27
<212> TYPE: DNA
<213> ORGANISM: artificial
<220> FEATURE:
<223> OTHER INFORMATION: Forward primer AKR1C1

<400> SEQUENCE: 43
gcagaggttc ctaaaagtaa agcttta                                       27

<210> SEQ ID NO 44
<211> LENGTH: 27
<212> TYPE: DNA
<213> ORGANISM: artificial
<220> FEATURE:
<223> OTHER INFORMATION: Reverse primer AKR1C1

<400> SEQUENCE: 44
acctgctcct cattattgta taaatga                                       27

<210> SEQ ID NO 45
<211> LENGTH: 24
<212> TYPE: DNA
<213> ORGANISM: artificial
<220> FEATURE:
<223> OTHER INFORMATION: Forward primer AKR1C2

<400> SEQUENCE: 45
cattgcatga ggtctgccag aagg                                          24

<210> SEQ ID NO 46
<211> LENGTH: 24
<212> TYPE: DNA
<213> ORGANISM: artificial
<220> FEATURE:
<223> OTHER INFORMATION: Reverse primer AKR1C2

<400> SEQUENCE: 46
cttagctgta gcttactgaa gtcg                                          24

<210> SEQ ID NO 47
<211> LENGTH: 24
```

```
<212> TYPE: DNA
<213> ORGANISM: artificial
<220> FEATURE:
<223> OTHER INFORMATION: Forward primer CYP1B1

<400> SEQUENCE: 47
atcaacaagg acctgaccag caga                                          24

<210> SEQ ID NO 48
<211> LENGTH: 24
<212> TYPE: DNA
<213> ORGANISM: artificial
<220> FEATURE:
<223> OTHER INFORMATION: Reverse primer CYP1B1

<400> SEQUENCE: 48
tcatttgggt tggccctgaa atcg                                          24

<210> SEQ ID NO 49
<211> LENGTH: 24
<212> TYPE: DNA
<213> ORGANISM: artificial
<220> FEATURE:
<223> OTHER INFORMATION: Forward primer FTH1P

<400> SEQUENCE: 49
ctttgaccgc gatgatgtgg cttt                                          24

<210> SEQ ID NO 50
<211> LENGTH: 24
<212> TYPE: DNA
<213> ORGANISM: artificial
<220> FEATURE:
<223> OTHER INFORMATION: Reverse primer FTH1P

<400> SEQUENCE: 50
tcagtttctc agcatgttcc ctct                                          24

<210> SEQ ID NO 51
<211> LENGTH: 24
<212> TYPE: DNA
<213> ORGANISM: artificial
<220> FEATURE:
<223> OTHER INFORMATION: Forward primer FTL

<400> SEQUENCE: 51
ttggatcttc atgccctggg ttct                                          24

<210> SEQ ID NO 52
<211> LENGTH: 24
<212> TYPE: DNA
<213> ORGANISM: artificial
<220> FEATURE:
<223> OTHER INFORMATION: Reverse primer FTL

<400> SEQUENCE: 52
agtcgtgctt gagagtgagc cttt                                          24

<210> SEQ ID NO 53
<211> LENGTH: 24
<212> TYPE: DNA
<213> ORGANISM: artificial
<220> FEATURE:
<223> OTHER INFORMATION: Forward primer G6PD

<400> SEQUENCE: 53
```
gaacctcatg gtgctgagat ttgc                                    24

<210> SEQ ID NO 54
<211> LENGTH: 24
<212> TYPE: DNA
<213> ORGANISM: artificial
<220> FEATURE:
<223> OTHER INFORMATION: Reverse primer G6PD

<400> SEQUENCE: 54
tgaggataac gcaggcgatg ttgt                                    24

<210> SEQ ID NO 55
<211> LENGTH: 24
<212> TYPE: DNA
<213> ORGANISM: artificial
<220> FEATURE:
<223> OTHER INFORMATION: Forward primer GCLM

<400> SEQUENCE: 55
atggcctgtt cagtccttgg agtt                                    24

<210> SEQ ID NO 56
<211> LENGTH: 24
<212> TYPE: DNA
<213> ORGANISM: artificial
<220> FEATURE:
<223> OTHER INFORMATION: Reverse primer GCLM

<400> SEQUENCE: 56
tcccagtaag gctgtaaatg ctcc                                    24

<210> SEQ ID NO 57
<211> LENGTH: 24
<212> TYPE: DNA
<213> ORGANISM: artificial
<220> FEATURE:
<223> OTHER INFORMATION: Forward primer NQO2

<400> SEQUENCE: 57
cacgaagaca ggagtcaatg gaga                                    24

<210> SEQ ID NO 58
<211> LENGTH: 24
<212> TYPE: DNA
<213> ORGANISM: artificial
<220> FEATURE:
<223> OTHER INFORMATION: Reverse primer NQO2

<400> SEQUENCE: 58
cggatgcaat ttcaggagca aagc                                    24

<210> SEQ ID NO 59
<211> LENGTH: 24
<212> TYPE: DNA
<213> ORGANISM: artificial
<220> FEATURE:
<223> OTHER INFORMATION: Forward primer SLC7A11

<400> SEQUENCE: 59
tatccctggc atttggacgc taca                                    24

<210> SEQ ID NO 60
<211> LENGTH: 24
<212> TYPE: DNA
<213> ORGANISM: artificial

```
<220> FEATURE:
<223> OTHER INFORMATION: Reverse primer SLC7A11

<400> SEQUENCE: 60
tgcccacagc tgtaatgagc ttga                                          24

<210> SEQ ID NO 61
<211> LENGTH: 24
<212> TYPE: DNA
<213> ORGANISM: artificial
<220> FEATURE:
<223> OTHER INFORMATION: Forward primer TXNRD1

<400> SEQUENCE: 61
ggtcctcaca ggattaaggc aaca                                          24

<210> SEQ ID NO 62
<211> LENGTH: 24
<212> TYPE: DNA
<213> ORGANISM: artificial
<220> FEATURE:
<223> OTHER INFORMATION: Reverse primer TXNRD1

<400> SEQUENCE: 62
tgcccaagta acgtggtctt tcac                                          24

<210> SEQ ID NO 63
<211> LENGTH: 24
<212> TYPE: DNA
<213> ORGANISM: artificial
<220> FEATURE:
<223> OTHER INFORMATION: Forward primer UGT1A1

<400> SEQUENCE: 63
acagaacttt ctgtgcgacg tggt                                          24

<210> SEQ ID NO 64
<211> LENGTH: 24
<212> TYPE: DNA
<213> ORGANISM: artificial
<220> FEATURE:
<223> OTHER INFORMATION: Reverse primer UGT1A1

<400> SEQUENCE: 64
agccagacag atgcagagct caat                                          24

<210> SEQ ID NO 65
<211> LENGTH: 24
<212> TYPE: DNA
<213> ORGANISM: artificial
<220> FEATURE:
<223> OTHER INFORMATION: Forward primer UGT1A9

<400> SEQUENCE: 65
gctttgccga ggcagggaag ctac                                          24

<210> SEQ ID NO 66
<211> LENGTH: 24
<212> TYPE: DNA
<213> ORGANISM: artificial
<220> FEATURE:
<223> OTHER INFORMATION: Reverse primer UGT1A9

<400> SEQUENCE: 66
atgagtttct ccaccaccga cctc                                          24
```

<210> SEQ ID NO 67
<211> LENGTH: 24
<212> TYPE: DNA
<213> ORGANISM: artificial
<220> FEATURE:
<223> OTHER INFORMATION: Forward primer YWHAZ

<400> SEQUENCE: 67
acagcagatg gctcgagaat acag                                              24

<210> SEQ ID NO 68
<211> LENGTH: 24
<212> TYPE: DNA
<213> ORGANISM: artificial
<220> FEATURE:
<223> OTHER INFORMATION: Reverse primer YWHAZ

<400> SEQUENCE: 68
tgctctctgc ttgtgaagca ttgg                                              24

<210> SEQ ID NO 69
<211> LENGTH: 24
<212> TYPE: DNA
<213> ORGANISM: artificial
<220> FEATURE:
<223> OTHER INFORMATION: Forward primer CD36

<400> SEQUENCE: 69
acagatgcag cctcatttcc acct                                              24

<210> SEQ ID NO 70
<211> LENGTH: 25
<212> TYPE: DNA
<213> ORGANISM: artificial
<220> FEATURE:
<223> OTHER INFORMATION: Reverse primer CD36

<400> SEQUENCE: 70
gggattcctt tcagattaac gtcgg                                             25

<210> SEQ ID NO 71
<211> LENGTH: 24
<212> TYPE: DNA
<213> ORGANISM: artificial
<220> FEATURE:
<223> OTHER INFORMATION: Forward primer CYP1A1

<400> SEQUENCE: 71
agtggcagat caaccatgac caga                                              24

<210> SEQ ID NO 72
<211> LENGTH: 24
<212> TYPE: DNA
<213> ORGANISM: artificial
<220> FEATURE:
<223> OTHER INFORMATION: Reverse primer CYP1A1

<400> SEQUENCE: 72
acaccttgtc gatagcacca tcag                                              24

<210> SEQ ID NO 73
<211> LENGTH: 24
<212> TYPE: DNA
<213> ORGANISM: artificial
<220> FEATURE:
<223> OTHER INFORMATION: Forward primer GCLC

<400> SEQUENCE: 73
aatgggcaat tgctgtctcc aggt                                          24

<210> SEQ ID NO 74
<211> LENGTH: 24
<212> TYPE: DNA
<213> ORGANISM: artificial
<220> FEATURE:
<223> OTHER INFORMATION: Reverse primer GCLC

<400> SEQUENCE: 74
aaagggagat gcagcactca aagc                                          24

<210> SEQ ID NO 75
<211> LENGTH: 24
<212> TYPE: DNA
<213> ORGANISM: artificial
<220> FEATURE:
<223> OTHER INFORMATION: Forward primer HMOX1

<400> SEQUENCE: 75
gggccagcaa caaagtgcaa gatt                                          24

<210> SEQ ID NO 76
<211> LENGTH: 24
<212> TYPE: DNA
<213> ORGANISM: artificial
<220> FEATURE:
<223> OTHER INFORMATION: Reverse primer HMOX1

<400> SEQUENCE: 76
tcgccaccag aaagctgagt gtaa                                          24

<210> SEQ ID NO 77
<211> LENGTH: 24
<212> TYPE: DNA
<213> ORGANISM: artificial
<220> FEATURE:
<223> OTHER INFORMATION: Forward primer NQO1

<400> SEQUENCE: 77
agtggctcca tgtactctct gcaa                                          24

<210> SEQ ID NO 78
<211> LENGTH: 24
<212> TYPE: DNA
<213> ORGANISM: artificial
<220> FEATURE:
<223> OTHER INFORMATION: Reverse primer NQO1

<400> SEQUENCE: 78
ttctccaggc gtttcttcca tcct                                          24

<210> SEQ ID NO 79
<211> LENGTH: 23
<212> TYPE: DNA
<213> ORGANISM: artificial
<220> FEATURE:
<223> OTHER INFORMATION: Forward primer S100A8

<400> SEQUENCE: 79
gggatgacct gaagaaattg cta                                           23

<210> SEQ ID NO 80

```
<211> LENGTH: 25
<212> TYPE: DNA
<213> ORGANISM: artificial
<220> FEATURE:
<223> OTHER INFORMATION: Reverse primer S100A8

<400> SEQUENCE: 80
tgttgatatc caactctttg aacca                                          25

<210> SEQ ID NO 81
<211> LENGTH: 24
<212> TYPE: DNA
<213> ORGANISM: artificial
<220> FEATURE:
<223> OTHER INFORMATION: Forward primer HSP90

<400> SEQUENCE: 81
tctgcctctg gtgatgagat ggtt                                           24

<210> SEQ ID NO 82
<211> LENGTH: 24
<212> TYPE: DNA
<213> ORGANISM: artificial
<220> FEATURE:
<223> OTHER INFORMATION: Reverse primer HSP90

<400> SEQUENCE: 82
tttccgaaga cgttccacaa aggc                                           24
```

METHOD FOR EVALUATING THE SENSITIZING POTENTIAL OF A TEST COMPOUND

The present invention relates to a method for evaluating the sensitizing potential of a test compound and a kit for implementing said method.

The perfume, cosmetics and pharmacy industries must remain competitive and effective and continue to regularly offer new products, with the constraint of complying with the human and environmental safety standards attached to their use. Contact allergy is one of the major risks associated with the use of such products.

Cutaneous contact allergy (or atopic dermatitis) is a major public health problem in humans. It represents a serious and restrictive environmental immunotoxic event, whose effects must be anticipated when marketing products that could induce it. Skin sensitization and, consequently, the associated allergic manifestation, is the result first of an interaction of an allergenic molecule with specialized epidermal cells, antigen-presenting cells (Langerhans cells, dendritic cells) and then, second, their presentation by these cells to $CD4^+$ and $CD8^+$ effector T cells. These T cells are the basis of the allergic and inflammatory reaction. However, the allergens, especially those that can be present in a fragrance, are small molecules that cannot be recognized directly. To be recognized, they must be associated beforehand with self proteins. Thus, it is the newly-formed heterodimeric complex in the skin that will finally be presented to T cells in the proximal lymph nodes. Accordingly, the ability of a chemical molecule (fragrance compound or cosmetic ingredient) to be associated with a protein of the user of this product is a prerequisite for the induction of the consecutive pathological skin reaction. This pathological skin reaction could be irritation, sensitization, or in the majority of cases, both irritation and sensitization.

Irritation is a reversible inflammatory reaction in living tissues by chemical action at the contact site. This is recognized by edema consecutive to the influx of fluid to the tissues, redness, heat and/or pain. In response to a chemical attack, keratinocytes of the epidermis and fibroblasts of the dermis are stimulated and release cytokines IL1, TNF alpha, IL6 and IL8, as well as mediators such as prostaglandins (PGE2) into the skin which will initiate the inflammatory response.

The delayed and immediate hypersensitivities that are the basis of sensitization involve the concept of "memory" which emphasizes their irreversible nature, unlike irritation. In this case as well, the mechanisms occur in two phases:

the first, called sensitization phase, during which the antigen/allergen is presented to the immune system and, in particular, to the T cells that record the molecular signal and regulate, via the cytokines produced, the other cell populations involved (B cells, T CD8, endothelial cells, macrophages, mast cells keratinocytes, etc.);

the second phase, called the effector phase, during which various skin cell populations will act via the chemical mediators responsible for pathologic disorders. In the case of immediate hypersensitivity, anaphylactic antibodies such as IgE are generated and bind mast cells and basophils, leading to the release of histamine, the main vector for allergic manifestations. In the case of delayed hypersensitivity, it is cytotoxic T cells (TCD8) that are responsible for skin lesions by destroying keratinocytes.

Thus, although from a histological point of view, sensitizing and irritant contact dermatitis are very similar, the immunological consequences analyzed at the cellular level are not necessarily similar. Consequently, it is important to have reliable methodologies for distinguishing them. An original predictive approach is even more necessary since currently no clear correlation has been demonstrated between a given molecular structure and allergenicity in the broadest sense of term.

So far, animals have been used to identify skin sensitizing molecules and the LLNA (local lymph node assay), based on the induced proliferation of lymph node lymphocytes after contact with the sensitizer, has been developed. This test was adopted as "Testing guideline 429" by the Organization for Economic Cooperation and Development (OECD) and is still considered as the standard test for determination of a sensitizing chemical agent.

The new European restrictions now require the use of methods that do not use animals and it is therefore vital to develop alternative methods for determining if a new composition or new product is likely to represent a risk for humans due to its sensitizing properties.

The Inventors have shown that in vivo recognition of a substance does not occur at the draining lymph node, as is generally accepted, but rather at the tissue where the substance comes into contact with the body, the skin in the present case. This would explain why some substances are sensitizing in one tissue and not in another, as is often observed. It therefore appears that it is the reaction in skin tissue that sends the message to the allergen-presenting cells: the dendritic cells will then transmit it to the T cells in the draining lymph node.

It is generally accepted that skin models are not sufficient to analyze sensitizing responses and it is necessary to have dendritic cells (EP 0857971).

The Inventors have now demonstrated that skin constitutes a sufficient model to show specific biomarkers for sensitization and/or irritation in humans and in mice, and that it is not necessary to add other types of cells if the identified genes are analyzed at a specific time. The EPISKIN model can thus be the standard tissue for evaluating the sensitizing nature of a test compound.

Moreover, the Inventors have shown that it was not sufficient to show an overexpression of only one of said biomarkers to conclude the sensitizing potential of a test compound, and that only studying at least six specific markers for sensitization would allow drawing conclusions about the sensitizing potential of a test compound.

Thus, the present invention relates to a method for evaluating the sensitizing potential of a test compound, comprising the steps of:

a) contacting a test compound with a biological sample;

b) determining the expression level of at least six genes chosen in the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (Interleukin-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (gelatinase-associated lipocalin), PDZK1IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD (P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9, YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQ01 (NAD(P)H dehydrogenase, quinone 1) and S100A8 (S100 calcium binding protein A8).

Preferably, said at least six genes are chosen in the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (gelatinase associated lipocalin), PDZK1IP1 (PDZK1 interacting protein interaction 1), P13 (peptidase inhibitor 3), PSME2 (proteasome activator subunit 2), SERPINB3 (serpin peptidase inhibitor member 3), AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9) and YWHAZ (tyrosine 3-monooxygenase/tryptophan 5-monooxygenase activation protein, zeta polypeptide), more preferably still chosen in the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (gelatinase associated lipocalin), PDZK1IP1 (PDZK1 interacting protein interaction 1), P13 (peptidase inhibitor 3 and SERPINB3 (serpin peptidase inhibitor member 3), and even more preferentially still chosen in the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein) IL18 (IL-18), HSP90 (heat shock 90 kDa protein), IL1R2 (interleukin-1 receptor type II), TPSAB1 (tryptase alpha/beta 1), or in the group made up of: CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3, PSME2 (proteasome activator subunit 2) and SERPINB3 (serpin peptidase inhibitor member 3)

Preferably, the method according to the present invention can also comprise another step c) for determining the sensitizing potential of a test compound.

Preferentially, said step c) can consist of a step of selecting said compound as presenting a sensitizing potential if the expression level of at least 6 of said genes is above a threshold value.

Preferably, the method according to the present invention is an in vitro method. As used here, the term "biological sample" refers to any solid or liquid sample from a subject.

Preferably, said biological sample is a skin sample.

In a particularly preferred manner, the skin sample is a skin sample reconstructed in vitro, such as, for example, the EpiSkin (EPISKIN, Lyon France), EpiDerm™ (MATEK Corporation, Ashland, Mass.) or SkinEthic™ RHE (SKI-NETHIC, Nice, France) model. Preferably, said skin sample reconstructed in vitro also comprises a keratin layer.

Even more preferably, the skin sample does not comprise other types of additional cells, and more preferentially no additional Langerhans cells.

The test compound can be a compound of various type, structure and origin, especially a biological compound, chemical compound, synthetic, etc.

The test compound can be any product present in the isolated form or mixed with other products. The test compound can be defined in terms of structure and/or composition or can be defined functionally. The test compound can be, for example, an isolated and structurally defined product, an isolated product of undefined structure, a mixture of known and characterized products or a composition comprising one or more products. One or more compounds can be tested in this way, mixed or separately.

Such compositions can be, for example, samples of a cosmetic or dermatological product.

Preferably, said test compound is suitable for use on the skin and may be used in a cosmetic or dermatological composition.

Preferentially, said method allows assessing the sensitizing potential of a test compound in humans, comprising a step b) of determining the expression level of at least six genes such as defined in Table 1, and preferably chosen in the group made up of: CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), P13 (peptidase inhibitor 3), PSME2 (proteasome activator subunit 2), and SERPINB3 (serpin peptidase inhibitor member 3).

"Sensitizing potential" means the risk for the test compound to provoke an immunological reaction when contacted with a mammal, preferably a human. Thus, sensitizing potential can be considered as the risk of developing a contact allergy to the test compound.

"Irritant potential" means the risk for the test compound to provoke a reversible inflammation of living tissue by chemical action at the contact site.

Preferably, the method according to the present invention allows evaluating whether the test compound is likely to induce a contact allergy or atopic dermatitis.

The present invention is particularly suited to identifying a large number of compounds. This simple and effective screening can be done in a very brief period of time. In particular, the methods described may be partially automated, thus allowing effective and simultaneous screening of diverse and numerous compounds, either in mixed or separate form.

Preferably, in the method according to the present invention, the expression level of each of said genes is determined by measuring the expression level of the polypeptides encoded by said gene or a fragment thereof, or by determining the expression level of the mRNA from said gene or a fragment thereof.

In one particularly preferred embodiment, the expression level of each of said at least six genes is determined by analysis of the expression of mRNA transcripts or mRNA precursors, such as a native RNA, of said gene. Said analysis can be done by preparing mRNA/cDNA from cells of a patient's biological sample, and hybridizing the mRNA/cDNA with a reference polynucleotide. The prepared mRNA/cDNA may be used in analysis by hybridization or amplification that includes, without being limiting, Southern and Northern analysis, PCR ("polymerase chain reaction"), such as quantitative PCR (Taqman) and the use of probes ("probe arrays") such as GeneChip® DNA matrices® (AFFYMETRIX).

Advantageously, the analysis of the mRNA expression transcript of each of said at least six genes involves a nucleic acid amplification process, such as, for example, RT-PCR (experimental method described in U.S. Pat. No. 4,683,202), ligase chain reaction (BARANY, *Proc. Natl. Acad. Sci. USA*, vol. 88, p: 189-193, 1991), self sustained sequence replication (GUATELLI et al., *Proc. Natl. Acad. Sci. USA*, vol. 87, p: 1874-1878, 1990) and transcriptional amplification system. (KWOH et al., *Proc. Natl. Acad. Sci. USA*, vol. 86, p: 1173-1177, 1989), "Q-Beta Replicase" (LIZARDI et al., *Biol. Technology*, vol. 6, p: 1197, 1988), "rolling circle replication" (U.S. Pat. No. 5,854,033) or any other nucleic acid amplification method, followed by a step of detecting the amplified molecules by techniques well known to the skilled person. These detection modes are particularly useful for detecting nucleic acid molecules in very small quantities. Thus, according to a preferred embodiment, the method according to the present invention comprises an additional step of amplifying the mRNA or cDNA of each of said six genes, the complementary sequence thereof or a fragment thereof.

Such as used here, amplification primers are defined as being a pair of nucleic acid molecules that can respectively pair with the 3' and 5' regions of a gene in a specific manner (positive and negative strands or vice versa) and encompassing a short region of said gene. Generally, amplification primers have a length of 10 to 30 nucleotides and allow amplifying a region of a length comprised between 50 and 200 nucleotides. Advantageously the primers used in the present invention are those listed in Table 1.

In another particularly preferred embodiment, the expression level of each of said at least six genes is determined by determining the expression level of the polypeptide encoded by said gene or a fragment thereof. Said analysis can be done by using an antibody (for example, a radiolabeled antibody, an antibody labeled with a chromophore, a fluorophore or an enzyme) an antibody derivative (for example, an antibody conjugated to a substrate or to a protein, or a ligand of a protein of a ligand/protein pair (for example biotin-streptavidin)) or an antibody fragment (for example, a single chain antibody, a hypervariable domain of an isolated antibody, etc.) which specifically binds the polypeptide encoded by said gene.

Said analyses can be done by many techniques known to the skilled person including, without being limiting, immunological tests based on the use of enzymatic activity ("enzyme immunoassay" EIA), immunological tests based on the use of radioactive isotopes (RIA), western blot analysis and ELISA ("enzyme linked immunosorbent assay") tests.

In the sense of the present invention, "polypeptide" means a sequence comprising at least two amino acids, and the terms "polypeptide", "peptide" and "protein" may be used interchangeably.

In the sense of the present invention, "mRNA or cDNA fragment" means a sequence of at least 50 nucleic acids, for example at least 100 or 150 nucleic acids, preferably at least 200 nucleic acids, for example at least 250 or 350 nucleic acids, and in a particularly preferred manner, a polypeptide [sic; nucleic acid sequence] of at least 400 nucleic acids.

In the sense of the present invention, "polypeptide fragment" means a sequence of at least 50 amino acids, for example at least 100 or 150 amino acids, preferably at least 200 amino acids, for example at least 250 or 350 amino acids, and in a particularly preferred manner, a polypeptide of at least 400 amino acids.

Preferably, the method according to the present invention also comprises a step of comparing the expression level of each of said at least six genes with a reference value. This reference value can serve as a positive and/or negative control.

A positive control can be conducted, for example, by comparing the expression level of said at least one gene in the presence of the test compound with the expression level of said at least one gene in the presence of a compound known to be sensitizing.

As an example of a compound known to be sensitizing, the following can be named: 2,4,6-trinitrobenzene sulfonic acid, p-phenylenediamine, dinitrochlorobenzene, benzaldehyde, resorcinol, tetramethylthiuram disulfide, oxazolone, chloroatranol, diphenylcyclopropenone, potassium dichromate, cinnamaldehyde, 2-bromo-2-(bromomethyl) glutaronitrile, glyoxal, saccharin, formaldehyde, trimellitic anhydride, methylchloroisothiazolinone, benzyl benzoate, alpha-hexyl cinnamaldehyde, eugenol, 2-mercaptobenzothiazole, isoeugenol, diphenylcyclopropenone (DCPP), lauryl gallate (LG), 3-3-dimethylaminopropylamine (3-DMAPA), cinnamaldehyde (CA), citral (Cal), 1,4-hydroquinone (HQ), glutaraldehyde (GA), 1,2-benzisothiazolin-3-one (Ben), phenylacetaldehyde (PA) and lilial (Li), preferably diphenylcyclopropenone, lauryl gallate, 1,4-hydroquinone and glutaraldehyde, and particularly preferably 1,4-hydroquinone.

Alternatively, in the present invention, a sensitizing compound can be used as a positive control, such as "fragrance mix".

A negative control can be conducted in the absence of the test compound or in the presence of a compound known to be non-sensitizing, such as, for example, olive oil, glycerol, cetyltrimethylammonium bromide (CTAB) and dipropylene glycol.

In the scope of the present invention, we will conclude that a test compound has a sensitizing potential if an overexpression of said gene is observed with regard to its expression level in the absence of said test compound.

"Overexpression" means a significantly higher level of said gene compared to its normal expression level. Preferably, overexpression means an expression level in a biological sample that is greater by at least 20% than the normal expression level of said gene, preferably greater by at least 50% than the normal expression level of said gene, and more particularly preferably greater by at least 90% than the normal expression level of said gene.

"Expression level in the absence of said test compound" or "normal level" is the expression level of said gene in a control sample potentially corresponding to the biological sample of a patient who does not present sensitization or, preferably, to the mean of the expression level of said gene in different control samples.

Preferably, step b) of said method for evaluating sensitizing potential comprises measuring the expression of at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 and more preferentially, at least 25 genes chosen in the group made up of the genes such as defined in Table 1.

Thus, one can conclude that a test compound has a sensitizing potential if there is an overexpression of at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 and more preferentially, at least 25 genes chosen in the group made up of genes such as defined in Table 1.

In a particularly preferred manner, step b) of said method for evaluating sensitizing potential comprises determining the expression of the following group of genes: AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD (P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQ01 (NAD(P)H dehydrogenase, quinone 1) PSME2 (proteasome activator subunit 2), and S100A8 (S100 calcium binding protein A8), preferably chosen in the group consisting of: AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9, PSME2 (proteasome activator subunit 2), and YWHAZ (tyrosine 3-monooxygenase/tryptophan 5-monooxygenase activation protein, zeta polypeptide).

In this particularly preferred embodiment, the test compound is determined to have sensitizing potential if at least 11 of said genes are overexpressed compared to a reference value.

In a particularly preferred manner, step b) of said method for evaluating sensitizing potential comprises determining the expression of at least one of the following group of genes: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3) and SERPINB3 (serpin peptidase inhibitor member 3), and even more preferentially, the group of genes BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), IL1R2 (interleukin-1 receptor type II), HSP90 (heat shock 90 kDa protein), and TPSAB1 (tryptase alpha/beta 1), or the group of genes CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3) and SERPINB3 (serpin peptidase inhibitor member 3).

In this particularly preferred embodiment, the test compound is determined to have sensitizing potential if at least 7 of said genes, preferably at least 8 of said genes are overexpressed compared to a reference value.

In one particular embodiment, step b) of said method for evaluating the sensitizing potential of a test compound comprises a step α) of determining the expression level of at least 10, preferably at least 11, 12, 13, 14, 15, 16 and still more preferentially of the following group of genes: AKR1B10 (aldo-keto reductase family 1, member B10), AKR1C1 (aldo-keto reductase family 1, member C1), AKR1C2 (aldo-keto reductase family 1, member C2), CTGF (connective tissue growth factor), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), IER3 (immediate early response 3), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQ01 (NAD(P)H dehydrogenase, quinone 1) and S100A8 (S100 calcium binding protein A8).

and optionally a step β) of measuring the expression level of at least 10, preferably 11, 12, 13, 14, 15, 16, 17, 18, 19 and more preferentially of the following group of genes: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), IL1R2 (interleukin-1 receptor type II), TPSAB1 (tryptase alpha/beta 1), HSP90 (heat shock 90 kDa protein), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), P13 (peptidase inhibitor 3), PSME2 (proteasome activator subunit 2) and SERPINB3 (serpin peptidase inhibitor member 3), and a step c) of determining the sensitizing potential of a test compound wherein the compound is determined to be sensitizing if:

the expression level of at least 7 genes measured in step α) is greater than a threshold value; and/or the expression level of at least 7 genes measured in step β) is greater than a limit value.

Preferably, step b) is done between 2 and 24 hours after step a), still more preferably between 4 and 18 hours after step a), preferentially between 5 and 7 hours after step a) and most preferably of all, 6 hours after step a).

Another aspect of the invention relates to a method for evaluating the sensitizing power of a test compound, comprising the following steps:

1) obtaining at least one test compound dilution, and
2) determining the sensitizing potential of said test compound at said at least one dilution by a method such as defined according to any one of the preceding claims.

"Sensitizing power" means the ability of a given compound to induce a sensitization reaction according to the concentration of said compound. Sensitizing power is dependent on the quantity of substance necessary to induce sensitization. Thus, the lower the sensitizing quantity necessary to induce a sensitizing response, the stronger the sensitizer is, and vice versa, the higher the sensitizing quantity necessary to induce a sensitizing response, the weaker the sensitizer is.

It is thus possible to perform a quantitative analysis of the sensitizing potential of a compound.

Preferably, said test compound is subject to successive dilutions. Thus, steps 1) and 2) will be done for each of the dilutions.

Preferably, said successive dilutions will allow determining the maximum dilution at which said test compound retains sensitizing potential.

Said method for evaluating the sensitizing power of a test compound can also comprise a step of evaluating the sensitizing power of the test compound.

Thus, the more a product retains a sensitizing potential after successive dilutions, the more powerful a sensitizer the test compound is.

Moreover, the sensitizing power of a test compound will also be a function of the irritant potential of said test compound. Thus, the fact that a test compound has an irritant potential increases the sensitizing power of said test compound.

Consequently, in one preferred embodiment, said method also comprises a step of determining the irritant potential of the test compound.

The irritant potential of a test compound can be evaluated by using, for example, the method described in French patent 1051638.

Thus, one can conclude that a product is extremely sensitizing (Extreme E), if:
it has a sensitizing potential at a dilution of 1/1000, and/or
it has a sensitizing potential at a dilution of 1/100, but does not have a sensitizing potential at 1/1000, and has an irritant potential.

Thus, one can conclude that a product is strongly sensitizing (Strong S), if:
it has a sensitizing potential at a dilution of 1/100, but does not have a sensitizing potential at 1/1000, or
it has a sensitizing potential at a dilution of 1/10, but does not have a sensitizing potential at 1/100 and has an irritant potential.

Thus, one can conclude that a product is moderately sensitizing (Moderate M), if:
it has a sensitizing potential at a dilution of 1/10, but does not have a sensitizing potential at 1/100, or it has a sensitizing potential at a dilution of 1/2, but does not have a sensitizing potential at dilutions below 1/2 and has an irritant potential.

Thus, one can conclude that a product is weakly sensitizing (weak W) if it does not have a sensitizing potential at dilutions below 1/2.

According to another aspect, the present invention relates to the use of at least one, preferably at least 2, at least 3, at least 4, at least 5, at least 6, at least 7 or at least 8 genes chosen in the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (gelatinase associated lipocalin), PDZK1IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), and YWHAZ (tyrosine 3-monooxygenase/tryptophan 5-monooxygenase activation protein, zeta polypeptide) for the in vitro evaluation of the sensitizing potential of a test compound.

The present invention also relates to a kit for the implementation of a method for in vitro evaluation of the sensitizing potential of a test compound, comprising means for determining the expression level of at least six genes selected from the group consisting of BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQ01 (NAD(P)H dehydrogenase, quinone 1) and S100A8 (S100 calcium binding protein A8).

Preferably, said kit will comprise at least six primer pairs each amplifying at least one gene chosen from the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), IL1R2 (interleukin-1 receptor type II), HSP90 (heat shock 90 kDa protein), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (gelatinase associated lipocalin), PDZK1IP1 (PDZK1 interacting protein interaction 1), P13 (peptidase inhibitor 3), PSME2 (proteasome activator subunit 2), SERPINB3 (serpin peptidase inhibitor member 3), AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQ01 (NAD(P)H dehydrogenase, quinone 1) and S100A8 (S100 calcium binding protein A8).

In a particularly preferred manner, said at least one primer pair is chosen in Table 1.

EXAMPLES

1) Demonstration of Biomarkers According to the Skinethic Protocol

Skin pieces of 1.07 $cm^2$ were purchased from EP1SKIN. Various substances were applied either in the liquid form (30 µL at different concentrations) or in the solid form (30 µL PBS or olive oil+30 µg or fewer to assess different powder concentrations) on the skin pieces. After an incubation of 15 min at room temperature, the skin pieces were washed with PBS (25 mL) and incubated 3 h, 6 h or 18 h at 37° C. in a $CO_2$ incubator. After incubation, the skin pieces were sampled with a punch and separated from the collagen support. They were then directly placed in a "Tri Reagent" solution (Ambion) (1 ml) and immediately dissociated mechanically.

cDNA Preparation

The tissues were placed in a "Tri Reagent" solution (Ambion) and mechanically crushed. The RNA was prepared according to the protocol described by the supplier with isopropanol precipitation. To prepare the cDNA, the total RNAs were pretreated with DNAse to remove genomic DNA contaminants. One to 5 µg of total RNA was used for the treatment, with RNAse-free DNAse, RNAsin (1 µL) and random primers (3 µg). The superscript III RT (1.5 mL at 200 U/µL) was then added. The cDNAs were then tested by RT-PCR.

Quantitative PCR

Real time quantitative PCR was performed using the SYBR Green technology of Roche LC480 cyclers. The primers were designed to cover the intron-exon junctions to prevent any traces of genomic DNA amplification. Amplification gives amplicons between 100 and 150 bp. All the primer pairs were qualified by digestion with restriction enzymes and analyzed by electrophoresis. PCR was performed on 10 µL by using the Sybr green 2×PCR mix from Roche in PCR plates from Roche. Target gene expression was measured after RNA normalization by means of four housekeeping genes, and the values are expressed by using the $C_T$ method, and expressed in additional expression rates with regard to a theoretical zero (User Bulletin no. 2, Applied Biosystems, December 1997).

Results

For this analysis, an application of 15 min followed by washing and a post-incubation of 6 h were done before biopsy and analysis of the gene transcription. The results are shown in Table 1.

TABLE 1 expression level of genes specific for sensitivity in the EPISKIN model

| Abbreviation | Gene name in French | English name | Accession number | Expression level in the absence of sensiting agent | Expression level in the presence of sensiting agent | Sens primer | Antisense primer |
|---|---|---|---|---|---|---|---|
| BRAK | CXC chimiokine ligand 14 | chemokine (C-X-C motif) ligand 14 | NM_004887.4 | 0.653688171 | 1.8 | AAGTACCCGCAC TGCGAGGAGAAG (SEQ ID NO: 1) | TTGGTGCTCTGCAGC TTGGGGTGC (SEQ ID NO: 2) |
| HSP90 | Protéine de choc thermique de 90kDa | Heat shock 90kDa protein | NM_005348.3 | 1.054321721 | 1.75 | TCTGCCTCTGGT GATGAGATGGTT (SEQ ID NO: 81) | TTTCCGAAGACGTTC CACAAAGGC (SEQ ID NO: 82) |
| CTSS | cathepsine S | cathepsin S | NM_004079.3 | 0.51868364 | 2.296020251 | TCATACGATCTG GGCATGAACCAC (SEQ ID NO: 3) | TGGGAACTCTCAGGG AACTCATCA (SEQ ID NO: 4) |
| DAPK2 | protéine kinase associée à la mort 2 | death-associated protein kinase 2 | NM_014326.3 | 1.012589915 | 1.454643548 | TTTCCTTCAGCA TCGTGTCCCTGT (SEQ ID NO: 5) | TGTCACTCTCACAGT TCCTCAGGT (SEQ ID NO: 6) |

TABLE 1-continued expression level of genes specific for sensitivity in the EPISKIN model

| Abbreviation | Gene name in French | English name | Accession number | Expression level in the absence of sensiting agent | Expression level in the presence of sensiting agent | Sens primer | Antisense primer |
|---|---|---|---|---|---|---|---|
| FABP4 | Proteine de fixation des acides gras 4 | fatty acid binding protein 4, adipocyte | NM_001442.2 | 0.844425344 | 2.920748581 | ACTGGGCCAGGA ATTTGACGAAGT (SEQ ID NO: 7) | TTTCTGCACATGTAC CAGGACACC (SEQ ID NO: 8) |
| HSP27 | Protéine de choc thermique de27kDa | heat shock 27kDa protein 1 | NM_001540.3 | 0.868543127 | 1.612936908 | TGCTTCACGCGG AAATACACGCT (SEQ ID NO: 9) | CTGGGATGGTGATCT CGTTGGACT (SEQ ID NO: 10) |
| IL18 | Interleukine 18 | Interleukin 18 (interferon-gamma-inducing factor) | NM_001562.2 | 1.190956418 | 2.309301387 | TCATTGACCAAG GAAATCGGCCTC (SEQ ID NO: 11) | AGCCATACCTCTAGG CTGGCTAT (SEQ ID NO: 12) |
| IL1R2 | Recepteur type II de l'interleukine 1 | interleukin 1 receptor, type II | NM_173343.1 | 1.280621228 | 1.9 | GCCAGCCTTGCA GGAGGACTCTG (SEQ ID NO: 13) | TTGCGGGTATGAGAT GAACGGCAG (SEQ ID NO: 14) |
| TPSAB1 | tryptase alpha/beta 1 | tryptase alpha/beta 1 | NM_003294.3 | 0.048878149 | 33.92776528 | ACGGCCCATACT GGATGCACTTCT (SEQ ID NO: 15) | CAGCAGCTGGTCCTG GTAGTAGA (SEQ ID NO: 16) |
| CXCR1 | Recepteur alpha de l'interleukin 8 | interleukin 8 receptor, alpha | NM_000634.2 | 1.442894074 | 3.492178966 | TATGAATCTGTCC CTGCCCTTC (SEQ ID NO: 17) | ACCTCATAGCAAACT GGACTGGAA (SEQ ID NO: 18) |
| DEFB1 | defensine, beta 1 | defensin, beta 1 | NM_005218.3 | 0.667424597 | 2.431463704 | TTCCTGAAATCCT GGGTGTTGCCT (SEQ ID NO: 19) | AGGCCTGTGAGAAA GTTACCACCT (SEQ ID NO: 20) |
| DHFR | dihydrofolate reductase | dihydrofolate reductase | NM_000791.3 | 1.033017625 | 2.6 | CTCATTTTCTTTC CAGAAGTCTAG (SEQ ID NO: 21) | TGCCACCAACTATCC AGACCATGT (SEQ ID NO: 22) |
| EHF | Facteur homologue ets | ets homologous factor | NM_012153.3 | 0.827499527 | 2.815783657 | TTGGCTCTCTCAT GTCCTTGGCTT (SEQ ID NO: 23) | AGGTATGACACTGTG GTAGGTGCT (SEQ ID NO: 24) |
| IVL | involucrine | involucrin | NM_005547.2 | 0.943876521 | 1.859505427 | TGCCCACAAAGG GAGAAGTATTGC (SEQ ID NO: 25) | TCTGGACACTGCGGG TGGTTATTT (SEQ ID NO: 26) |
| KRT4 | keratine 4 | keratin 4 | NM_002272.2 | 0.925148858 | 1.35742071 | TCACATATGTCCC TTCCCAGTCCA (SEQ ID NO: 27) | TGCCGGGTGTTGGAG AAGTAGTTT (SEQ ID NO: 28) |
| MELANA | melane-A | melan-A | NM_005511.1 | 0.763327598 | 2.7 | TCTTACTGCTCAT CGGCTGTTGGT (SEQ ID NO: 29) | TGAAGAGACACTTTG CTGTCCCGA (SEQ ID NO: 30) |
| NGAL | Gelatinase des neutrophiles | lipocalin 2 | NM_005564.3 | 1.069357565 | 1.8 | GTGAGCACCAAC TACAACCAGCAT (SEQ ID NO: 31) | AGTTCCGAAGTCAGC TCCTTGGTT (SEQ ID NO: 32) |

TABLE 1-continued expression level of genes specific for sensitivity in the EPISKIN model

| Abbreviation | Gene name in French | English name | Accession number | Expression level in the absence of sensiting agent | Expression level in the presence of sensiting agent | Sens primer | Antisense primer |
|---|---|---|---|---|---|---|---|
| PDZK11P1 | Protéine d'interaction PDZK1 | PDZK1 interacting protein 1 | NM_005764.3 | 0.705479404 | 2.3 | CAATCGCCTTTGC AGTCAACCACT (SEQ ID NO: 33) | ACCAGGACTCCATCT GCCTTGTTT (SEQ ID NO: 34) |
| PI3 | Inhibiteur de peptidase | peptidase inhibitor 3, skin-derived | NM_002638.3 | 1.19471567 | 2.5 | TCTTGATCGTGGT GGTGTTCCTCA (SEQ ID NO: 35) | GACTGGCTCTTGCGC TTTGACTTT (SEQ ID NO: 36) |
| PSME2 | Sous unité activatrice du proteasome 2 | proteasome activator subunit 2 (PA28 beta) | NM_002818.2 | 1.066067422 | 1.9 | TCCCTCAATGTG GCTGACTTGACT (SEQ ID NO: 37) | TCTCATTCCCAGGGA GAAATCCAC (SEQ ID NO: 38) |
| SERPINB3 | Membre 3 des Inhibiteurs de la serpine peptidase | serpin peptidase inhibitor, clade B (ovalbumin), member 3 | NM_006919.2 | 0.462228737 | 4.366336795 | ACTCCTGGGTGG AAAGTCAAACGA (SEQ ID NO: 39) | ACTCCTGGGTGGAA AGTCAAACGA (SEQ ID NO: 40) |
| AKR1B10 | Membre B10 de la famille des aldo-keto reductases | aldo-keto reductase family 1, member B10 (aldose reductase) | NM_020299.4 | 1.219844195 | 1.9 | AAGATGATAAAGG TAATGCCATCG (SEQ ID NO: 41) | AGCTTCTCGATCTGG AAGTGGCTG (SEQ ID NO: 42) |
| AKR1C1 | Membre C1 de la famille des aldo-keto reductases | aldo-keto reductase family 1, member C1 | NM_001353.5 | 1.587681403 | 3.432182344 | GCAGAGGTTCCTA AAAGTAAAGCTTT A (SEQ ID NO: 43) | ACCTGCTCCTCATTA TTGTATAAATGA (SEQ ID NO: 44) |
| AKR1C2 | Membre C2 de la famille des aldo-keto reductases | aldo-keto reductase family 1, member C2 | NM_001354.4 | 0.686185206 | 3.101161617 | CATTGCATGAGGT CTGCCAGAAGG (SEQ ID NO: 45) | CTTAGCTGTAGCTTA CTGAAGTCG (SEQ ID NO: 46) |
| CYP1B1 | cytochrome P450, famille 1, sous famille B, polypeptide 1 | cytochrome P450, family 1, subfamily B, polypeptide 1 | NM_000104.3 | 0.751299588 | 17.37117803 | ATCAACAAGGACC TGACCAGCAGA (SEQ ID NO : 47) | TCATTTGGGTTGGCC CTGAAATCG (SEQ ID NO: 48) |
| FTH1P | Polypeptide lourd de la ferritine, 1 | ferritin, heavy polypeptide 1 | NM_002032.2 | 1.032878604 | 1.942318842 | CTTTGACCGCGAT GATGTGGCTTT (SEQ ID NO: 49) | TCAGTTTCTCAGCAT GTTCCCTCT (SEQ ID NO: 50) |
| FTL | Polypeptide léger de la ferritine, 1 | ferritin, light polypeptide | NM_000146.3 | 0.681444874 | 2.940199851 | TTGGATCTTCATG CCCTGGGTTCT (SEQ ID NO: 51) | AGTCGTGCTTGAGAG TGAGCCTTT (SEQ ID NO: 52) |
| G6PD | glucose-6-phosphate dehydrogenase | glucose-6-phosphate dehydrogenase | NM_000402.3 | 0.581030262 | 1.7 | GAACCTCATGGTG CTGAGATTTGC (SEQ ID NO: 53) | TGAGGATAACGCAG GCGATGTTGT (SEQ ID NO: 54) |

TABLE 1-continued expression level of genes specific for sensitivity in the EPISKIN model

| Abbreviation | Gene name in French | English name | Accession number | Expression level in the absence of sensiting agent | Expression level in the presence of sensiting agent | Sens primer | Antisense primer |
|---|---|---|---|---|---|---|---|
| GCLM | Sous unité modificatrice de la glutamate-cysteine ligase | glutamate-cysteine ligase, modifier subunit | NM_002061.2 | 0.874803304 | 5.083406994 | ATGGCCTGTTCAGTCCTTGGAGTT (SEQ ID NO: 55) | TCCCAGTAAGGCTGTAAATGCTCC (SEQ ID NO: 56) |
| NQO2 | NAD(P)H dehydrogenase des quinones2 | NAD(P)H dehydrogenase, quinone 2 | NM_000904.3 | 1.170224823 | 2.8 | CACGAAGACAGGAGTCAATGGAGA (SEQ ID NO: 57) | CGGATGCAATTTCAGGAGCAAAGC (SEQ ID NO: 58) |
| SLC7A11 | Membre 11 de la famille 7 des porteurs de molécules solubles | solute carrier family 7, (cationic amino acid transporter, y+ system) member 11 | NM_014331.3 | 0.502347786 | 5.088930603 | TATCCCTGGCATTTGGACGCTACA (SEQ ID NO: 59) | TGCCCACAGCTGTAATGAGCTTGA (SEQ ID NO: 60) |
| TXNRD1 | thioredoxine reductase 1 | thioredoxin reductase 1 | NM_182729.1 | 0.725407592 | 3.70757292 | GGTCCTCACAGGATTAAGGCAACA (SEQ ID NO: 61) | TGCCCAAGTAACGTGGTCTTTCAC (SEQ ID NO: 62) |
| UGT1A1 | Polypeptide A1 de la famille des UDP glucuronosyltransferase 1 | UDP glucuronosyltransferase 1 family, polypeptide A1 | NM_000463.2 | 0.527392251 | 1.408908304 | ACAGAACTTTCTGTGCGACGTGGT (SEQ ID NO: 63) | AGCCAGACAGATGCAGAGCTCAAT (SEQ ID NO: 64) |
| UGT1A9 | Polypeptide A9 de la famille des UDP glucuronosyltransferase 1 | UDP glucuronosyltransferase 1 family, polypeptide A9 | NM_021027.2 | 0.568212175 | 1.402794916 | GCTTTGCCGAGGCAGGGAAGCTAC (SEQ ID NO: 65) | ATGAGTTTCTCCACCACCGACCTC (SEQ ID NO: 66) |
| YWHAZ | Polypeptide zeta de la proteine d'activation de tyrosine 3-monooxygenase/ tryptophan 5-monooxygenase polypeptide | tyrosine 3-monooxygenase/ tryptophan 5-monooxygenase activation protein, zeta polypeptide | NM_001135702.1 | 1.154023086 | 3.1 | ACAGCAGATGGCTCGAGAATACAG (SEQ ID NO: 67) | TGCTCTCTGCTTGTGAAGCATTGG (SEQ ID NO: 68) |
| CD36 | CD36 molecule | CD36 molecule (thrombospondin receptor) | NM_001127444.1 | 0.640243459 | 5.375531509 | ACAGATGCAGCCTCATTTCCACCT (SEQ ID NO: 69) | GGGATTCCTTTCAGATTAACGTCGG (SEQ ID NO: 70) |
| CYP1A1 | cytochrome P450, famille 1, sous famille A, polypeptide 1 | cytochrome P450, family 1, subfamily A, polypeptide 1 | NM_000499.3 | 0.549457486 | 3.763056606 | AGTGGCAGATCAACCATGACCAGA (SEQ ID NO: 71) | ACACCTTGTCGATAGCACCATCAG (SEQ ID NO: 72) |

TABLE 1-continued expression level of genes specific for sensitivity in the EPISKIN model

| Abbreviation | Gene name in French | English name | Accession number | Expression level in the absence of sensiting agent | Expression level in the presence of sensiting agent | Sens primer | Antisense primer |
|---|---|---|---|---|---|---|---|
| GCLC | Sous unité catalitique de la glutamate-cysteine ligase | glutamate-cysteine ligase, catalytic subunit | NM_001498.2 | 0.905634705 | 2.728685624 | AATGGGCAATTGC TGTCTCCAGGT (SEQ ID NO: 73) | AAAGGGAGATGCAGC ACTCAAAGC (SEQ ID NO: 74) |
| HMOX1 | heme oxygenase 1 | heme oxygenase (decycling) 1 | NM_002133.1 | 0.76137536 | 1.461320376 | GGGCCAGCAACAA AGTGCAAGATT (SEQ ID NO: 75) | TCGCCACCAGAAAGC TGAGTGTAA (SEQ ID NO: 76) |
| NQO1 | NAD(P)H dehydrogenase, des quinones 1 | NAD(P)H dehydrogenase, quinone 1 | NM_001025434.1 | 0.740574662 | 1.948391073 | AGTGGCTCCATGT ACTCTCTGCAA (SEQ ID NO: 77) | TTCTCCAGGCGTTTC TTCCATCCT (SEQ ID NO: 78) |
| S100A8 | Protéine de fixation du calcium S100 A8 | S100 calcium binding protein A8 | NM_002964.3 | 0.970410479 | 1.890390064 | GGGATGACCTGAA GAAATTGCTA (SEQ ID NO: 79) | TGTTGATATCCAACT CTTTGAACCA (SEQ ID NO: 80) |

Moreover, 35 substances classified according to their characteristics (non-irritant (non -IRR), non-sensitizer (NS), irritant (IRR) or sensitizing by using the official classification of Extreme (E), Strong (S), Moderate (M) and Weak (W) were tested at different doses (Table 2(a) and Table 2(b)). For analysis, the dose permitting the maximum response without inducing too much tissue destruction (corrosion) was selected.

| Class | Name | CAS# |
|---|---|---|
| S | Hydroquinone | 123-31-9 |
| S | 2-aminophenol | 95-55-6 |
| E | 4-Nitrobenzylbromide (electrophile) | 100-11-8 |
| S | 2,4,6-Trinitrobenzene sulfonic acid | 2508-19-2 |
| S | p-Phenylenediamine | 106-50-3 |
| M | Citral | 5392-40-5 |
| S | Dinitrochlorobenzene | 97-00-7 |
| M | Benzaldehyde | 100-52-7 |
| W | Resorcinol | 108-46-3 |
| M | Benzisothiazolin-3-one (Benzisothiazolinone) | 2634-33-5 |
| M | Tetramethylthiuram disulfide | 137-26-8 |
| S | Oxazolone | 15646-46-5 |
| S | Chloroatranol | 57074-21-2 |
| E | Diphenylcyclopropenone | 886-38-4 |
| S | Potassium Dichromate | 7778-50-9 |
| M | cinnamaldehyde | 104-55-2 |
| S | 2-Bromo-2-(bromomethyl)glutaronitrile | 35691-65-7 |
| M | Glyoxal | 107-22-2 |
| M | Saccharine | 6485-34-3 |
| S | Formaldehyde | 50-00-0 |
| M | Trimellitic anhydride | 552-30-7 |
| E | Methylchloroisothiazolinone | 26172-55-4 |
| M | Phenyl Acetaldehyde | 122-78-1 |
| W | Benzyl benzoate | 120-51-4 |
| W | Lilial | 80-5406 |
| W | alpha-Hexyl cinnamaldehyde | 101-86-0 |
| W | Eugenol | 97-53-0 |
| M | 2-mercaptobenzothiazole | 149-30-4 |
| S | Glutaraldehyde | 111-30-8 |
| M | Isoeugenol | 97-54-1 |
| NS | Dipropylene Glycol | 25265-71-8 |
| NS | Glycerol | 56-81-5 |
| NS | Cetyl trimethylammonium bromide | 57-09-0 |
| NS | Limonen | 5989-54-8 |
| IRR | Lactic acid (cys pos) | 598-82-3 |
| IRR | Sodium lauryl sulfate | 151-21-3 |

Three groups of biomarkers were tested on the samples, those specific for irritation, those represented by the ARE gene family (genes under the control of ARE "antioxidant responsive element promoters", i.e., AKR1B10, AKR1C1, AKR1C2, CYP1B1, FTH1P, FTL, G6PD, GCLM, NQO2, SLC7A11, TXNRD1, UGT1A1, UGT1A9, YWHAZ, CD36, CYP1A1, GCLC, HMOX1, NQO1, PSME2 and S100A8 genes) and another group of genes specific for sensitization, notably for sensitizing substances that do not induce ARE genes.

Irritants for which the expression of the IL-8 gene is 50 times greater than the control and that induce a non-specific expression of ARE genes were retested at lower doses.

The results are presented in Tables 2 and 3, with a code according to the degree of overexpression of the genes. If the expression is greater than 1.3 compared to the control, a grade of 1 is given; if this expression is lower, the grade is 0. Note that, preferably, if the number of ARE genes is greater than 11, one can conclude that the substance is certainly sensitizing. For substances that do not strongly induce ARE genes, the other group of sensitization genes is analyzed.

Observe that, preferably, if at least 8 of these genes are overexpressed, then the substance is clearly sensitizing.

Preferably, said test is done both on the group of ARE genes and the group of "non-ARE" genes.

TABLE 2

| Classe | Chemical | CAS # | Abrev | FAPB4 | CD36 | EHF | HSP27 | IVL | DAPK2 | KRT4 | NGAL | S100A8 | DEFB1 |
|---|---|---|---|---|---|---|---|---|---|---|---|---|---|
| S | Hydroquinone | 123-31-9 | HQ | 0 | 0 | 1 | 0 | 1 | 0 | 0 | 0 | 1 | 1 |
| E | 4-Nitrobenzylbromide (electrophile) | 100-11-8 | NBB | 1 | 1 | 0 | 0 | 1 | 0 | 0 | 0 | 1 | 1 |
| S | 2,4,6-Trinitrobenze sulfonic acid | 2508-19-2 | TNBS | 0 | 1 | 0 | 1 | 0 | 0 | 1 | 0 | 0 | 0 |
| S | p-Phenylenediamine | 106-50-3 | PPD | 0 | 1 | 1 | 0 | 1 | 0 | 0 | 0 | 0 | 0 |
| M | Citral | 5392-40-5 | CT | 1 | 0 | 1 | 0 | 1 | 0 | 0 | 0 | 1 | 1 |
| S | Dinitrochlorobenzene | 97-00-7 | DNCB | 1 | 1 | 0 | 0 | 1 | 1 | 1 | 1 | 1 | 1 |
| M | Benzaldehyde | 100-52-7 | BZA | 1 | 0 | 0 | 1 | 1 | 1 | 0 | 1 | 1 | 1 |
| W | Resorcinol | 108-46-3 | RSC | 0 | 0 | 0 | 1 | 0 | 1 | 1 | 1 | 0 | 0 |
| M | Benzisothiazolin-3-one (Benzisothiazolinone) | 2634-33-5 | BIT | 1 | 1 | 1 | 0 | 1 | 1 | 1 | 1 | 0 | 0 |
| M | Disulfur TétraMéthylThiurame | 137-26-8 | TMDT | 1 | 0 | 0 | 1 | 1 | 1 | 1 | 1 | 1 | 1 |
| S | Oxazolone | 15646-46-5 | Oxa | 1 | 0 | 0 | 1 | 1 | 0 | 1 | 1 | 1 | 1 |
| S | ChloroAtranol | 57074-21-2 | ChlAtr | 0 | 0 | 0 | 1 | 0 | 0 | 0 | 1 | 0 | 1 |
| E | Diphenylcyclopropen one | 886-38-4 | DPCP | 1 | 1 | 1 | 0 | 1 | 0 | 1 | 1 | 0 | 0 |
| S | Potassium Dichromate | 7778-50-9 | K2Cr2O7 | 1 | 1 | 1 | 0 | 0 | 0 | 1 | 1 | 1 | 1 |
| M | Cinnamic Aldehyde | 104-55-2 | CA | 1 | 1 | 1 | 1 | 1 | 1 | 1 | 0 | 1 | 1 |
| S | 2-Bromo-2-(bromomethyl)glutaronitrile | 35691-65-7 | BBMG | 1 | 0 | 0 | 1 | 1 | 1 | 1 | 1 | 1 | 1 |
| M | Glyoxal | 107-22-2 | GLX | 0 | 1 | 1 | 1 | 1 | 1 | 1 | 0 | 1 | 1 |
| M | Saccharine | 6485-34-3 | Sac | 0 | 0 | 1 | 0 | 1 | 0 | 0 | 1 | 1 | 1 |
| S | Formaldehyde | 50-00-0 | FA | 0 | 1 | 1 | 1 | 1 | 0 | 1 | 1 | 0 | 0 |
| M | Trimellitic anhydride | 552-30-7 | TMA | 1 | 0 | 0 | 1 | 1 | 0 | 1 | 1 | 1 | 1 |
| E | MethylChloroIsothiazolinone | 26172-55-4 | MCI | 1 | 0 | 1 | 0 | 1 | 0 | 0 | 0 | 0 | 1 |
| M | Phenyl Acetaldehyde | 122-78-1 | PA | 1 | 1 | 1 | 1 | 0 | 0 | 0 | 0 | 1 | 0 |
| W | Benzyl benzoate | 120-51-4 | BB | 1 | 1 | 1 | 0 | 1 | 0 | 1 | 1 | 0 | 0 |
| W | Lilial | 80-5406 | LI | 1 | 0 | 0 | 1 | 1 | 1 | 0 | 1 | 1 | 1 |
| W | alpha-Hexyl CinnAmaldehyde | 101-86-0 | HCA | 1 | 0 | 0 | 1 | 0 | 0 | 0 | 0 | 1 | 1 |
| W | Eugenol | 97-53-0 | Eug | 0 | 0 | 0 | 1 | 1 | 1 | 1 | 1 | 1 | 1 |
| M | 2mercaptobenzothiazole | 149-30-4 | MBT | 0 | 0 | 1 | 0 | 1 | 1 | 1 | 0 | 0 | 0 |
| S | Glutaraldehyde | 111-30-8 | GA | 0 | 0 | 1 | 0 | 1 | 1 | 0 | 0 | 0 | 0 |
| M | Isoeugenol | 97-54-1 | IE | 0 | 0 | 1 | 1 | 1 | 1 | 0 | 0 | 0 | 1 |
| NS | Dipropylene Glycol | 25265-71-8 | DPG | 1 | 0 | 1 | 0 | 1 | 0 | 1 | 0 | 0 | 0 |
| NS | Glycerol | 56-81-5 | Glyc | 0 | 1 | 0 | 0 | 0 | 0 | 0 | 0 | 0 | 1 |
| NS | Cetyl trimethylammonium bromide | 57-09-0 | CTAB | 0 | 1 | 1 | 0 | 1 | 0 | 0 | 1 | 0 | 0 |
| NS | Limonen | 5989-54-8 | LIM | 1 | 0 | 1 | 0 | 1 | 0 | 0 | 1 | 0 | 0 |
| IRR | Acide Lactique (pos cys) | 598-82-3 | LA | 0 | 0 | 0 | 1 | 0 | 1 | 0 | 0 | 0 | 0 |
| IRR | Sodium Lauryl Sulfate | 151-21-3 | SLS | 0 | 0 | 0 | 1 | 0 | 0 | 0 | 0 | 0 | 0 |

TABLE 2-continued

| Classe | Chemical | IL18 | P13 | CXCR1 | TPSAB1 | IL1R2 | BRAK | SERP1NB3 | MELANA | CTSS | DHFR | PDZKIIP1 | TOTAL |
|---|---|---|---|---|---|---|---|---|---|---|---|---|---|
| S | Hydroquinone | 1 | 1 | 1 | 0 | 1 | 0 | 1 | 0 | 1 | 0 | 0 | 10 |
| E | 4-Nitrobenzylbromide (electrophile) | 1 | 0 | 0 | 1 | 1 | 1 | 0 | 0 | 0 | 0 | 1 | 10 |
| S | 2,4,6-Trinitrobenze sulfonic acid | 1 | 0 | 1 | 0 | 1 | 1 | 0 | 1 | 0 | 0 | 1 | 9 |
| S | p-Phenylenediamine | 1 | 1 | 1 | 0 | 0 | 0 | 1 | 0 | 0 | 0 | 0 | 7 |
| M | Citral | 0 | 1 | 0 | 0 | 0 | 0 | 1 | 1 | 0 | 0 | 0 | 8 |
| S | Dinitrochlorobenzene | 1 | 1 | 1 | 1 | 1 | 1 | 1 | 1 | 0 | 0 | 1 | 18 |
| M | Benzaldehyde | 1 | 1 | 0 | 1 | 1 | 1 | 0 | 1 | 0 | 0 | 1 | 14 |
| W | Resorcinol | 1 | 0 | 0 | 0 | 0 | 1 | 0 | 1 | 0 | 1 | 0 | 8 |
| M | Benzisothiazolin-3-one (Benzisothiazolinone) | 0 | 0 | 1 | 0 | 0 | 0 | 1 | 0 | 1 | 0 | 0 | 10 |
| M | Disulfur TétraMéthylThiurame | 0 | 1 | 0 | 0 | 1 | 1 | 0 | 1 | 0 | 0 | 1 | 13 |
| S | Oxazolone | 0 | 1 | 1 | 1 | 1 | 1 | 1 | 1 | 1 | 0 | 0 | 15 |
| S | ChloroAtranol | 0 | 1 | 0 | 0 | 1 | 0 | 0 | 0 | 0 | 0 | 1 | 6 |
| E | Diphenylcyclopropen one | 0 | 0 | 1 | 0 | 0 | 0 | 1 | 0 | 0 | 0 | 0 | 8 |
| S | Potassium Dichromate | 1 | 0 | 1 | 1 | 1 | 1 | 1 | 1 | 0 | 1 | 1 | 16 |
| M | Cinnamic Aldehyde | 1 | 1 | 0 | 1 | 0 | 1 | 1 | 0 | 1 | 0 | 1 | 16 |
| S | 2-Bromo-2-(bromomethyl)glutaronitrile | 0 | 1 | 1 | 1 | 0 | 0 | 1 | 1 | 0 | 0 | 0 | 13 |
| M | Glyoxal | 1 | 0 | 0 | 1 | 1 | 1 | 0 | 1 | 0 | 0 | 1 | 14 |
| M | Saccharine | 1 | 1 | 1 | 1 | 1 | 0 | 1 | 0 | 0 | 0 | 1 | 12 |
| S | Formaldehyde | 0 | 0 | 1 | 1 | 1 | 1 | 1 | 0 | 1 | 0 | 0 | 12 |
| M | Trimellitic anhydride | 1 | 1 | 1 | 1 | 0 | 0 | 1 | 0 | 0 | 0 | 0 | 12 |
| E | MethylChloroIsothiazolinone | 0 | 0 | 1 | 1 | 1 | 0 | 0 | 1 | 1 | 0 | 0 | 10 |
| M | Phenyl Acetaldehyde | 1 | 1 | 0 | 1 | 0 | 0 | 1 | 0 | 1 | 1 | 0 | 11 |
| W | Benzyl benzoate | 1 | 0 | 0 | 0 | 0 | 0 | 1 | 0 | 0 | 1 | 0 | 9 |
| W | Lilial | 0 | 1 | 0 | 0 | 0 | 0 | 0 | 1 | 1 | 1 | 0 | 11 |
| W | alpha-Hexyl CinnAmaldehyde | 0 | 1 | 0 | 0 | 0 | 1 | 0 | 1 | 0 | 0 | 1 | 9 |
| W | Eugenol | 0 | 0 | 0 | 0 | 0 | 0 | 0 | 0 | 1 | 0 | 0 | 8 |
| M | 2mercaptobenzothiazole | 1 | 0 | 1 | 0 | 1 | 0 | 0 | 0 | 1 | 0 | 0 | 8 |
| S | Glutaraldehyde | 1 | 0 | 1 | 0 | 0 | 0 | 1 | 0 | 1 | 0 | 0 | 7 |
| M | Isoeugenol | 1 | 0 | 0 | 0 | 0 | 0 | 0 | 1 | 0 | 0 | 0 | 7 |
| NS | Dipropylene Glycol | 0 | 0 | 0 | 0 | 0 | 0 | 0 | 0 | 0 | 1 | 0 | 5 |
| NS | Glycerol | 1 | 0 | 0 | 0 | 1 | 0 | 1 | 0 | 0 | 0 | 0 | 5 |
| NS | Cetyl trimethylammonium bromide | 0 | 0 | 0 | 0 | 0 | 0 | 1 | 0 | 0 | 0 | 0 | 5 |
| NS | Limonen | 0 | 0 | 0 | 0 | 0 | 0 | 0 | 0 | 0 | 0 | 0 | 4 |
| IRR | Acide Lactique (pos cys) | 0 | 0 | 0 | 0 | 1 | 0 | 0 | 0 | 0 | 0 | 0 | 3 |
| IRR | Sodium Lauryl Sulfate | 0 | 0 | 0 | 0 | 1 | 0 | 0 | 0 | 0 | 0 | 0 | 2 |

TABLE 2-continued

| Classe | Chemical | GCLC | HMOX1 | NQO1 | FTL | FTH1P | TXNRDI | UGT1A1 | UGT1A9 | AKR1C1 | ARK1B10 | CYP1B1 | CYP1A1# |
|---|---|---|---|---|---|---|---|---|---|---|---|---|---|
| S | Hydroquinone | 1 | 1 | 1 | 1 | 1 | 1 | 1 | 1 | 1 | 0 | 1 | 1 |
| E | 4-Nitrobenzylbromide (electrophile) | 1 | 1 | 1 | 1 | 1 | 1 | 1 | 1 | 1 | 1 | 1 | 1 |
| S | 2,4,6-Trinitrobenze sulfonic acid | 1 | 1 | 1 | 1 | 1 | 1 | 1 | 1 | 1 | 1 | 1 | 1 |
| S | p-Phenylenediamine | 1 | 1 | 1 | 1 | 1 | 1 | 1 | 1 | 1 | 1 | 1 | 1 |
| M | Citral | 1 | 0 | 1 | 1 | 1 | 1 | 0 | 1 | 1 | 1 | 0 | 0 |
| S | Dinitrochlorobenzene | 1 | 0 | 1 | 1 | 1 | 1 | 0 | 1 | 1 | 0 | 1 | 1 |
| M | Benzaldehyde | 0 | 1 | 1 | 1 | 1 | 0 | 1 | 1 | 0 | 0 | 1 | 0 |
| W | Resorcinol | 1 | 1 | 1 | 1 | 1 | 1 | 0 | 0 | 1 | 0 | 0 | 0 |
| M | Benzisothiazolin-3-one (Benzisothiazolinone) | 1 | 0 | 1 | 1 | 1 | 1 | 0 | 0 | 1 | 0 | 1 | 1 |
| M | Disulfur TétraMéthylThiurame | 1 | 1 | 1 | 1 | 1 | 1 | 0 | 0 | 1 | 1 | 0 | 0 |
| S | Oxazolone | 0 | 0 | 1 | 1 | 1 | 1 | 0 | 1 | 0 | 0 | 1 | 0 |
| S | ChloroAtranol | 0 | 0 | 1 | 1 | 1 | 0 | 0 | 0 | 1 | 1 | 1 | 1 |
| E | Diphenylcyclopropen one | 1 | 1 | 1 | 1 | 1 | 1 | 0 | 1 | 1 | 0 | 1 | 0 |
| S | Potassium Dichromate | 0 | 1 | 0 | 0 | 1 | 1 | 0 | 0 | 1 | 0 | 0 | 1 |
| M | Cinnamic Aldehyde | 1 | 0 | 0 | 0 | 0 | 0 | 1 | 1 | 0 | 1 | 1 | 0 |
| S | 2-Bromo-2-(bromomethyl)glutaronitrile | 1 | 1 | 1 | 1 | 1 | 1 | 0 | 1 | 1 | 0 | 0 | 0 |
| M | Glyoxal | 0 | 1 | 0 | 1 | 1 | 1 | 1 | 0 | 0 | 0 | 1 | 0 |
| M | Saccharine | 0 | 1 | 0 | 1 | 0 | 0 | 0 | 1 | 1 | 0 | 0 | 1 |
| S | Formaldehyde | 1 | 0 | 0 | 1 | 1 | 1 | 0 | 0 | 0 | 0 | 0 | 0 |
| M | Trimellitic anhydride | 0 | 0 | 1 | 1 | 1 | 0 | 0 | 0 | 0 | 0 | 0 | 0 |
| E | MethylChloroIsothiazolinone | 1 | 0 | 1 | 1 | 1 | 1 | 0 | 1 | 1 | 0 | 0 | 0 |
| M | Phenyl Acetaldehyde | 0 | 0 | 0 | 0 | 0 | 0 | 0 | 1 | 0 | 0 | 1 | 0 |
| W | Benzyl benzoate | 1 | 0 | 0 | 0 | 0 | 1 | 0 | 1 | 0 | 0 | 1 | 0 |
| W | Lilial | 0 | 0 | 0 | 1 | 0 | 0 | 0 | 0 | 1 | 1 | 0 | 1 |
| W | alpha-Hexyl CinnAmaldehyde | 0 | 0 | 1 | 1 | 1 | 0 | 0 | 0 | 1 | 1 | 0 | 0 |
| W | Eugenol | 1 | 1 | 0 | 1 | 1 | 0 | 1 | 0 | 0 | 0 | 0 | 0 |
| M | 2mercaptobenzothiazole | 1 | 0 | 0 | 1 | 0 | 1 | 1 | 0 | 1 | 0 | 1 | 0 |
| S | Glutaraldehyde | 1 | 1 | 1 | 0 | 0 | 1 | 1 | 1 | 1 | 0 | 0 | 0 |
| M | Isoeugenol | 1 | 0 | 1 | 1 | 1 | 1 | 0 | 0 | 1 | 1 | 0 | 0 |
| NS | Dipropylene Glycol | 1 | 0 | 0 | 0 | 0 | 0 | 0 | 1 | 0 | 0 | 1 | 0 |
| NS | Glycerol | 0 | 0 | 0 | 0 | 0 | 1 | 1 | 0 | 0 | 0 | 0 | 0 |
| NS | Cetyl trimethylammonium bromide | 0 | 0 | 0 | 0 | 0 | 0 | 0 | 0 | 0 | 0 | 1 | 0 |
| NS | Limonen | 1 | 0 | 0 | 1 | 0 | 0 | 0 | 0 | 1 | 0 | 1 | 0 |
| IRR | Acide Lactique (pos cys) | 0 | 0 | 1 | 0 | 0 | 0 | 0 | 0 | 0 | 0 | 1 | 0 |
| IRR | Sodium Lauryl Sulfate | 0 | 0 | 0 | 1 | 1 | 0 | 0 | 0 | 0 | 0 | 0 | 0 |

TABLE 2-continued

| Classe | Chemical | NQO2 | SLC7A11 | GCLM | G6PD | YWHAZ | IER3 | CTGF | PSME2 | AKR1C2 | TOTAL |
|---|---|---|---|---|---|---|---|---|---|---|---|
| S | Hydroquinone | 1 | 1 | 1 | 1 | 1 | 0 | 0 | 1 | 1 | 18 |
| E | 4-Nitrobenzylbromide (electrophile) | 1 | 1 | 1 | 1 | 0 | 1 | 1 | 0 | 1 | 19 |
| S | 2,4,6-Trinitrobenze sulfonic acid | 1 | 1 | 1 | 1 | 0 | 1 | 0 | 0 | 1 | 18 |
| S | p-Phenylenediamine | 1 | 1 | 1 | 0 | 1 | 0 | 0 | 1 | 1 | 18 |
| M | Citral | 1 | 1 | 1 | 0 | 0 | 1 | 1 | 1 | 1 | 15 |
| S | Dinitrochlorobenzene | 1 | 1 | 1 | 0 | 0 | 0 | 1 | 0 | 1 | 14 |
| M | Benzaldehyde | 0 | 1 | 1 | 1 | 0 | 1 | 1 | 0 | 1 | 13 |
| W | Resorcinol | 1 | 1 | 1 | 0 | 0 | 0 | 1 | 0 | 1 | 12 |
| M | Benzisothiazolin-3-one (Benzisothiazolinone) | 0 | 1 | 1 | 0 | 1 | 0 | 0 | 0 | 1 | 12 |
| M | Disulfur TétraMéthylThiurame | 1 | 1 | 1 | 0 | 0 | 0 | 1 | 0 | 1 | 13 |
| S | Oxazolone | 1 | 1 | 1 | 0 | 0 | 1 | 1 | 0 | 1 | 12 |
| S | ChloroAtranol | 1 | 0 | 1 | 1 | 0 | 0 | 1 | 1 | 1 | 13 |
| E | Diphenylcyclopropen one | 0 | 1 | 1 | 0 | 1 | 0 | 0 | 0 | 1 | 13 |
| S | Potassium Dichromate | 1 | 1 | 1 | 0 | 0 | 0 | 1 | 1 | 1 | 11 |
| M | Cinnamic Aldehyde | 0 | 1 | 0 | 1 | 1 | 1 | 1 | 0 | 0 | 10 |
| S | 2-Bromo-2-(bromomethyl)glutaronitrile | 1 | 1 | 1 | 0 | 0 | 0 | 0 | 0 | 1 | 12 |
| M | Glyoxal | 0 | 1 | 1 | 1 | 0 | 0 | 1 | 0 | 1 | 11 |
| M | Saccharine | 1 | 0 | 1 | 1 | 1 | 1 | 0 | 1 | 1 | 12 |
| S | Formaldehyde | 0 | 1 | 1 | 1 | 0 | 0 | 0 | 0 | 0 | 7 |
| M | Trimellitic anhydride | 1 | 1 | 0 | 0 | 0 | 0 | 0 | 0 | 1 | 6 |
| E | MethylChloroIsothiazolinone | 0 | 1 | 1 | 0 | 0 | 1 | 0 | 0 | 1 | 11 |
| M | Phenyl Acetaldehyde | 0 | 0 | 0 | 0 | 1 | 0 | 0 | 0 | 0 | 3 |
| W | Benzyl benzoate | 0 | 1 | 1 | 0 | 1 | 0 | 0 | 0 | 0 | 7 |
| W | Lilial | 0 | 1 | 0 | 0 | 0 | 1 | 0 | 0 | 0 | 6 |
| W | alpha-Hexyl CinnAmaldehyde | 1 | 0 | 1 | 1 | 0 | 0 | 1 | 1 | 1 | 11 |
| W | Eugenol | 1 | 1 | 1 | 0 | 0 | 0 | 1 | 0 | 1 | 10 |
| M | 2mercaptobenzothiazole | 0 | 1 | 1 | 0 | 0 | 0 | 0 | 0 | 1 | 9 |
| S | Glutaraldehyde | 0 | 1 | 1 | 0 | 1 | 0 | 0 | 1 | 0 | 11 |
| M | Isoeugenol | 0 | 1 | 1 | 0 | 0 | 0 | 0 | 0 | 1 | 10 |
| NS | Dipropylene Glycol | 0 | 0 | 1 | 0 | 1 | 0 | 0 | 0 | 0 | 5 |
| NS | Glycerol | 0 | 1 | 0 | 0 | 0 | 0 | 0 | 0 | 0 | 3 |
| NS | Cetyl trimethylammonium bromide | 0 | 0 | 0 | 0 | 1 | 0 | 0 | 0 | 1 | 2 |
| NS | Limonen | 0 | 0 | 0 | 0 | 1 | 0 | 0 | 0 | 1 | 6 |
| IRR | Acide Lactique (pos cys) | 0 | 0 | 0 | 1 | 0 | 1 | 0 | 0 | 0 | 4 |
| IRR | Sodium Lauryl Sulfate | 0 | 1 | 0 | 0 | 0 | 1 | 0 | 0 | 0 | 4 |

In order to be able to evaluate the sensitizing power of the compounds, a selection of compounds was subjected to successive dilutions in order to be tested again for their sensitizing potential, as shown in Table 3.

| | DAPK2 | CTSS | EHF | NGAL | S100A8 | DEFB1 | P13 | CXCR1 | IL1R2 | FABP4 | IVL | CD36 | HSP27 |
|---|---|---|---|---|---|---|---|---|---|---|---|---|---|
| methyl-chloro-isothiazolinone | | | | | | | | | | | | | |
| MCIT-50% | 1.0 | 2.0 | 5.8 | 2.2 | 1.6 | 3.0 | 2.2 | 1.6 | 5.1 | 1.5 | 5.0 | 0.8 | 1.3 |
| NUMBER OF GENES | 0 | 1 | 1 | 1 | 1 | 1 | 1 | 1 | 1 | 1 | 1 | 0 | 1 |
| MCIT-10% | 0.8 | 1.1 | 3.7 | 2.2 | 1.5 | 2.6 | 2.1 | 1.0 | 3.2 | 1.4 | 3.7 | 0.7 | 1.1 |
| NUMBER OF GENES | 0 | 0 | 1 | 1 | 1 | 1 | 1 | 0 | 1 | 1 | 1 | 0 | 0 |
| MCIT-1% | 0.8 | 1.3 | 1.8 | 1.2 | 1.2 | 1.7 | 1.6 | 1.2 | 1.7 | 1.3 | 2.2 | 0.8 | 0.8 |
| NUMBER OF GENES | 0 | 0 | 1 | 0 | 0 | 1 | 1 | 0 | 1 | 1 | 1 | 0 | 0 |
| MCIT-0.1% | 0.6 | 0.7 | 1.1 | 2.2 | 1.0 | 1.1 | 1.9 | 1.4 | 1.7 | 1.0 | 1.3 | 1.1 | 1.3 |
| NUMBER OF GENES | 0 | 0 | 0 | 1 | 0 | 0 | 1 | 1 | 1 | 0 | 0 | 0 | 0 |
| diphenyl cyclopropenone | | | | | | | | | | | | | |
| DPCP-50% | 1.2 | 0.9 | 2.1 | 0.6 | 1.1 | 1.4 | 1.2 | 1.5 | 1.2 | 0.9 | 1.4 | 1.0 | 1.1 |
| NUMBER OF GENES | 0 | 0 | 1 | 0 | 0 | 1 | 0 | 1 | 0 | 0 | 1 | 0 | 0 |
| DPCP-10% | 1.2 | 0.9 | 1.2 | 1.2 | 1.1 | 1.1 | 1.1 | 1.2 | 0.9 | 1.0 | 1.3 | 1.0 | 1.0 |
| NUMBER OF GENES | 0 | 0 | 0 | 0 | 0 | 0 | 0 | 0 | 0 | 0 | 0 | 0 | 0 |
| DPCP-1% | 1.2 | 1.0 | 1.2 | 1.0 | 1.2 | 1.3 | 1.1 | 1.5 | 1.4 | 0.8 | 1.3 | 1.3 | 1.0 |
| NUMBER OF GENES | 0 | 0 | 0 | 0 | 0 | 0 | 0 | 1 | 1 | 0 | 0 | 0 | 0 |
| DPCP-0.1% | 1.3 | 1.6 | 0.8 | 1.1 | 1.0 | 1.2 | 1.1 | 2.3 | 1.1 | 1.1 | 1.3 | 0.8 | 0.9 |
| NUMBER OF GENES | 0 | 1 | 0 | 0 | 0 | 0 | 0 | 1 | 0 | 0 | 0 | 0 | 0 |

| | KRT4 | BRAK | SERPINB3 | MELANA | HSP90 | PDZK1iP1 | IL18 | DHFR | TOTAL SENS | GCLC | NQO1 | FTL |
|---|---|---|---|---|---|---|---|---|---|---|---|---|
| methyl-chloro-isothiazolinone | | | | | | | | | | | | |
| MCIT-50% | 1.1 | 0.3 | 3.2 | 0.4 | 3.5 | 0.8 | 0.9 | 0.6 | | 16.5 | 4.6 | 17.0 |
| NUMBER OF GENES | 0 | 0 | 1 | 0 | 1 | 0 | 0 | 0 | 13 | 1 | 1 | 1 |

-continued

|  |  |  |  |  |  |  |  |  |  |  |  |
|---|---|---|---|---|---|---|---|---|---|---|---|
| MCIT-10% | 1.6 | 0.3 | 2.7 | 0.6 | 2.0 | 0.9 | 0.7 | 0.7 |  | 14.8 | 6.8 | 11.0 |
| NUMBER OF GENES | 1 | 0 | 1 | 0 | 1 | 0 | 0 | 0 | 11 | 1 | 1 | 1 |
| MCIT-1% | 1.2 | 0.5 | 1.7 | 0.7 | 1.3 | 0.9 | 0.8 | 0.8 |  | 5.3 | 5.1 | 4.4 |
| NUMBER OF GENES | 0 | 0 | 1 | 0 | 1 | 0 | 0 | 0 | 8 | 1 | 1 | 1 |
| MCIT-0.1% | 2.4 | 1.5 | 1.6 | 0.3 | 1.4 | 1.3 | 1.3 | 1.2 |  | 1.7 | 1.8 | 1.2 |
| NUMBER OF GENES | 1 | 1 | 1 | 0 | 1 | 1 | 0 | 0 | 9 | 1 | 1 | 0 |
| diphenyl cyclopropenone |  |  |  |  |  |  |  |  |  |  |  |  |
| DPCP-50% | 0.5 | 0.3 | 1.2 | 1.2 | 2.7 | 0.8 | 0.9 | 0.9 |  | 7.2 | 6.2 | 4.9 |
| NUMBER OF GENES | 0 | 0 | 0 | 0 | 1 | 0 | 0 | 0 | 5 | 1 | 1 | 1 |
| DPCP-10% | 0.7 | 0.7 | 1.0 | 1.5 | 1.2 | 1.0 | 0.8 | 0.9 |  | 5.0 | 4.3 | 3.2 |
| NUMBER OF GENES | 0 | 0 | 0 | 1 | 0 | 0 | 0 | 0 | 4 | 1 | 1 | 1 |
| DPCP-1% | 1.0 | 0.7 | 1.3 | 0.4 | 1.2 | 1.2 | 1.2 | 0.8 |  | 1.7 | 2.0 | 1.5 |
| NUMBER OF GENES | 0 | 0 | 0 | 0 | 0 | 0 | 0 | 0 | 2 | 1 | 1 | 1 |
| DPCP-0.1% | 1.0 | 1.2 | 0.9 | 0.8 | 1.0 | 0.9 | 0.6 | 0.9 |  | 1.0 | 1.8 | 1.4 |
| NUMBER OF GENES | 0 | 0 | 0 | 0 | 0 | 0 | 0 | 0 | 2 | 0 | 1 | 1 |

|  | FTH1P | AKR1B10 | AKR1C2 | AKR1C1 | CYP1B1 | CYP1A1 | TXNRD1 | HMOX1 | UGT1A1 | UGT1A9 |
|---|---|---|---|---|---|---|---|---|---|---|
| methyl-chloro-isothiazolinone |  |  |  |  |  |  |  |  |  |  |
| MCIT-50% | 5.7 | 1.0 | 10.6 | 24.8 | 177.9 | 3855.0 | 45.1 | 22.4 | 1.3 | 1.7 |
| NUMBER OF GENES | 1 | 0 | 1 | 1 | 1 | 1 | 1 | 1 | 1 | 1 |
| MCIT-10% | 3.8 | 1.3 | 9.6 | 27.0 | 49.5 | 852.8 | 29.7 | 14.3 | 1.4 | 1.2 |
| NUMBER OF GENES | 1 | 1 | 1 | 1 | 1 | 1 | 1 | 1 | 1 | 0 |
| MCIT-1% | 2.0 | 1.8 | 6.6 | 15.6 | 35.0 | 217.3 | 10.9 | 3.1 | 2.1 | 1.5 |
| NUMBER OF GENES | 1 | 1 | 1 | 1 | 1 | 1 | 1 | 1 | 1 | 1 |
| MCIT-0.1% | 1.1 | 1.4 | 1.5 | 1.3 | 49.0 | 115.5 | 1.5 | 1.5 | 2.1 | 1.0 |
| NUMBER OF GENES | 0 | 0 | 1 | 0 | 1 | 1 | 1 | 1 | 1 | 0 |
| diphenyl cyclopropenone |  |  |  |  |  |  |  |  |  |  |
| DPCP-50% | 2.5 | 1.9 | 7.3 | 19.3 | 32.5 | 13.9 | 23.5 | 10.0 | 3.4 | 1.9 |
| NUMBER OF GENES | 1 | 1 | 1 | 1 | 1 | 1 | 1 | 1 | 1 | 1 |
| DPCP-10% | 2.3 | 2.0 | 5.0 | 9.8 | 68.6 | 87.6 | 10.0 | 2.2 | 4.6 | 3.1 |
| NUMBER OF GENES | 1 | 1 | 1 | 1 | 1 | 1 | 1 | 1 | 1 | 1 |
| DPCP-1% | 1.3 | 1.2 | 2.1 | 3.6 | 40.5 | 45.7 | 3.7 | 1.6 | 2.5 | 1.8 |
| NUMBER OF GENES | 0 | 0 | 1 | 1 | 1 | 1 | 1 | 1 | 1 | 1 |
| DPCP-0.1% | 1.2 | 1.1 | 1.6 | 0.9 | 2.6 | 9.2 | 1.6 | 0.9 | 2.1 | 1.1 |
| NUMBER OF GENES | 0 | 0 | 1 | 0 | 1 | 1 | 1 | 0 | 1 | 0 |

|  | NQO2 | SLC7A11 | GCLM | AHR | TOTAL ARE | SENS >1.3 | ARE >1.3 |  |  |
|---|---|---|---|---|---|---|---|---|---|
| methyl-chloro-isothiazolinone |  |  |  |  |  |  |  |  |  |
| MCIT-50% | 2.0 | 29.1 | 21.8 | 1.0 |  |  |  |  |  |
| NUMBER OF GENES | 1 | 1 | 1 | 0 | 15 | 13 | 15 | Sensitizing | EXTREME |
| MCIT-10% | 1.8 | 26.5 | 19.1 | 1.3 |  |  |  |  |  |
| NUMBER OF GENES | 1 | 1 | 1 | 1 | 16 | 11 | 16 | Sensitizing |  |
| MCIT-1% | 1.6 | 12.8 | 11.3 | 1.1 |  |  |  |  |  |
| NUMBER OF GENES | 1 | 1 | 1 | 0 | 16 | 8 | 16 | Sensitizing |  |
| MCIT-0.1% | 1.4 | 2.3 | 1.5 | 1.6 |  |  |  |  |  |
| NUMBER OF GENES | 0 | 1 | 1 | 1 | 11 | 9 | 11 | Sensitizing |  |
| diphenyl |  |  |  |  |  |  |  |  |  | cyclopropenone

|  |  |  |  |  |  |  |  |  |  |
|---|---|---|---|---|---|---|---|---|---|
| DPCP-50% | 1.5 | 24.3 | 13.8 | 1.4 |  |  |  |  |  |
| NUMBER OF GENES | 1 | 1 | 1 | 1 | 17 | 5 | 17 | Sensitizing | EXTREME |
| DPCP-10% | 1.7 | 13.5 | 7.3 | 0.8 |  |  |  |  |  |
| NUMBER OF GENES | 1 | 1 | 1 | 0 | 16 | 4 | 16 | Sensitizing |  |
| DPCP-1% | 1.4 | 2.8 | 2.4 | 0.6 |  |  |  |  |  |
| NUMBER OF GENES | 1 | 1 | 1 | 0 | 14 | 2 | 14 | Sensitizing |  |
| DPCP-0.1% | 1.1 | 1.7 | 1.3 | 0.9 |  |  |  |  |  |
| NUMBER OF GENES | 0 | 1 | 0 | 0 | 8 | 2 | 8 | Sensitizing |  |

|  | DAPK2 | CTSS | EHF | NGAL | S100A8 | DEFB1 | P13 | CXCR1 | IL1R2 | FABP4 | IVL | CD36 | HSP27 |
|---|---|---|---|---|---|---|---|---|---|---|---|---|---|
| 2-aminophenol |  |  |  |  |  |  |  |  |  |  |  |  |  |
| 2-aminophenol-50% | 1.0 | 1.3 | 1.7 | 1.8 | 1.3 | 1.9 | 1.5 | 2.3 | 2.0 | 1.1 | 1.8 | 0.7 | 1.0 |
| NUMBER OF GENES | 0 | 1 | 1 | 1 | 1 | 1 | 1 | 1 | 1 | 0 | 1 | 0 | 0 |
| 2-aminophenol-10% | 1.0 | 1.2 | 1.5 | 1.9 | 1.2 | 1.8 | 1.4 | 1.5 | 1.8 | 1.1 | 1.8 | 0.5 | 1.1 |
| NUMBER OF GENES | 0 | 0 | 1 | 1 | 0 | 1 | 1 | 1 | 1 | 0 | 1 | 0 | 0 |
| 2-aminophenol-1% | 0.9 | 1.4 | 1.4 | 1.5 | 1.2 | 1.4 | 1.2 | 2.0 | 1.3 | 0.7 | 1.3 | 0.6 | 0.8 |
| NUMBER OF GENES | 0 | 1 | 1 | 1 | 0 | 1 | 0 | 1 | 0 | 0 | 1 | 0 | 0 |
| 2-aminophenol-0.1% | 1.0 | 1.4 | 1.2 | 1.1 | 1.4 | 1.1 | 1.3 | 1.0 | 1.0 | 0.9 | 0.9 | 0.9 | 0.8 |
| NUMBER OF GENES | 0 | 1 | 0 | 0 | 1 | 0 | 0 | 0 | 0 | 0 | 0 | 0 | 0 |
| Hydroquinone |  |  |  |  |  |  |  |  |  |  |  |  |  |
| hydroquinone-50% | 1.0 | 1.6 | 1.5 | 1.3 | 1.4 | 2.0 | 1.7 | 2.9 | 1.5 | 1.4 | 2.6 | 0.8 | 1.3 |
| NUMBER OF GENES | 0 | 1 | 1 | 0 | 1 | 1 | 1 | 1 | 1 | 1 | 1 | 0 | 0 |
| hydroquinone-10% | 1.2 | 0.8 | 1.2 | 2.0 | 1.4 | 1.5 | 1.4 | 2.2 | 1.4 | 1.2 | 1.8 | 0.7 | 1.0 |
| NUMBER OF GENES | 0 | 0 | 0 | 1 | 0 | 1 | 0 | 1 | 0 | 0 | 1 | 0 | 0 |
| hydroquinone-1% | 1.2 | 1.2 | 1.1 | 1.7 | 1.4 | 1.1 | 1.2 | 2.8 | 1.2 | 1.1 | 1.5 | 0.7 | 0.9 |
| NUMBER OF GENES | 0 | 0 | 0 | 1 | 1 | 0 | 0 | 1 | 0 | 0 | 1 | 0 | 0 |
| hydroquinone-0.1% | 1.1 | 0.7 | 1.2 | 1.5 | 1.1 | 1.7 | 1.1 | 2.9 | 1.3 | 1.1 | 1.6 | 0.7 | 0.8 |
| NUMBER OF GENES | 0 | 0 | 0 | 1 | 0 | 1 | 0 | 1 | 0 | 0 | 1 | 0 | 0 |

|  | KRT4 | BRAK | SERPINB3 | MELANA | HSP90 | PDZK1iP1 | IL18 | DHFR | TOTAL SENS | GCLC | NQO1 |
|---|---|---|---|---|---|---|---|---|---|---|---|
| 2-aminophenol |  |  |  |  |  |  |  |  |  |  |  |
| 2-aminophenol-50% | 1.7 | 0.3 | 1.4 | 0.2 | 1.5 | 1.0 | 0.9 | 0.9 |  | 4.0 | 3.3 |
| NUMBER OF GENES | 1 | 0 | 1 | 0 | 1 | 0 | 0 | 0 | 12 | 1 | 1 |
| 2-aminophenol-10% | 1.7 | 0.3 | 1.2 | 0.2 | 1.5 | 1.0 | 0.9 | 0.9 |  | 2.3 | 2.5 |
| NUMBER OF GENES | 1 | 0 | 0 | 0 | 1 | 0 | 0 | 0 | 9 | 1 | 1 |
| 2-aminophenol-1% | 1.1 | 0.5 | 1.2 | 0.5 | 1.2 | 1.0 | 0.8 | 0.9 |  | 2.2 | 1.1 |
| NUMBER OF GENES | 0 | 0 | 0 | 0 | 0 | 0 | 0 | 0 | 6 | 1 | 0 |
| 2-aminophenol-0.1% | 1.7 | 0.8 | 1.3 | 1.1 | 1.0 | 1.0 | 1.1 | 1.2 |  | 1.1 | 0.9 |
| NUMBER OF GENES | 1 | 0 | 1 | 0 | 0 | 0 | 0 | 0 | 4 | 0 | 0 |
| Hydroquinone |  |  |  |  |  |  |  |  |  |  |  |
| hydroquinone-50% | 1.1 | 0.8 | 1.1 | 1.6 | 1.8 | 1.0 | 0.9 | 1.1 |  | 2.4 | 2.8 |
| NUMBER OF GENES | 0 | 0 | 0 | 1 | 1 | 0 | 0 | 0 | 11 | 1 | 1 |
| hydroquinone-10% | 1.2 | 0.8 | 1.1 | 0.9 | 1.2 | 1.0 | 0.9 | 0.7 |  | 1.5 | 1.5 |
| NUMBER OF GENES | 0 | 0 | 0 | 0 | 0 | 0 | 0 | 0 | 4 | 1 | 1 |
| hydroquinone-1% | 1.5 | 0.8 | 1.0 | 0.7 | 1.1 | 1.0 | 0.8 | 0.8 |  | 1.3 | 1.3 |
| NUMBER OF GENES | 1 | 0 | 0 | 0 | 0 | 0 | 0 | 0 | 5 | 0 | 0 |
| hydroquinone-0.1% | 2.0 | 0.7 | 1.1 | 0.7 | 1.3 | 1.2 | 0.8 | 0.4 |  | 1.3 | 1.2 |
| NUMBER OF GENES | 1 | 0 | 0 | 0 | 0 | 0 | 0 | 0 | 5 | 0 | 0 |

-continued

|  | FTL | FTH1P | AKR1B10 | AKR1C2 | AKR1C1 | CYP1B | CYP1A1 | TXNRD1 | HMOX1 | UGT1A1 |
|---|---|---|---|---|---|---|---|---|---|---|
| 2-aminophenol | | | | | | | | | | |
| 2-aminophenol-50% | 3.5 | 2.0 | 1.3 | 3.3 | 8.6 | 37.7 | 66.5 | 6.4 | 1.9 | 2.1 |
| NUMBER OF GENES | 1 | 1 | 1 | 1 | 1 | 1 | 1 | 1 | 1 | 1 |
| 2-aminophenol-10% | 2.5 | 1.5 | 1.1 | 3.4 | 9.3 | 45.1 | 122.0 | 7.6 | 1.7 | 1.8 |
| NUMBER OF GENES | 1 | 1 | 0 | 1 | 1 | 1 | 1 | 1 | 1 | 1 |
| 2-aminophenol-1% | 2.1 | 1.2 | 0.9 | 1.2 | 4.3 | 15.6 | 14.6 | 4.8 | 1.4 | 1.6 |
| NUMBER OF GENES | 1 | 0 | 0 | 0 | 1 | 1 | 1 | 1 | 1 | 1 |
| 2-aminophenol-0.1% | 1.0 | 0.9 | 0.8 | 1.1 | 1.2 | 5.3 | 7.1 | 3.0 | 1.1 | 0.9 |
| NUMBER OF GENES | 0 | 0 | 0 | 0 | 0 | 1 | 1 | 1 | 0 | 0 |
| Hydroquinone | | | | | | | | | | |
| hydroquinone-50% | 3.5 | 2.1 | 1.1 | 3.7 | 3.5 | 49.5 | 57.8 | 7.9 | 3.5 | 1.9 |
| NUMBER OF GENES | 1 | 1 | 0 | 1 | 1 | 1 | 1 | 1 | 1 | 1 |
| hydroquinone-10% | 1.9 | 1.4 | 1.0 | 1.8 | 2.6 | 17.1 | 33.2 | 2.6 | 1.2 | 1.5 |
| NUMBER OF GENES | 1 | 1 | 0 | 1 | 1 | 1 | 1 | 1 | 0 | 1 |
| hydroquinone-1% | 1.5 | 1.3 | 1.0 | 1.3 | 2.0 | 7.1 | 15.4 | 2.1 | 1.0 | 1.4 |
| NUMBER OF GENES | 1 | 0 | 0 | 0 | 1 | 1 | 1 | 1 | 0 | 0 |
| hydroquinone-0.1% | 1.5 | 1.2 | 0.9 | 0.7 | 1.2 | 1.8 | 8.0 | 2.3 | 1.1 | 1.7 |
| NUMBER OF GENES | 1 | 0 | 0 | 0 | 0 | 1 | 1 | 1 | 0 | 1 |

|  | UGT1A9 | NQO2 | SLC7A11 | GCLM | AHR | TOTAL ARE | SENS >1.3 | ARE >1.3 | | |
|---|---|---|---|---|---|---|---|---|---|---|
| 2-aminophenol | | | | | | | | | | |
| 2-aminophenol-50% | 0.4 | 1.3 | 6.0 | 4.7 | 1.3 | | | | | |
| NUMBER OF GENES | 0 | 0 | 1 | 1 | 0 | 14 | 12 | 14 | Sensitizing | STRONG |
| 2-aminophenol-10% | 1.2 | 1.4 | 3.8 | 4.6 | 0.7 | | | | | |
| NUMBER OF GENES | 0 | 1 | 1 | 1 | 0 | 14 | 9 | 14 | Sensitizing | |
| 2-aminophenol-1% | 1.0 | 1.1 | 3.2 | 3.5 | 0.6 | | | | | |
| NUMBER OF GENES | 0 | 0 | 1 | 1 | 0 | 10 | 6 | 10 | Sensitizing | |
| 2-aminophenol-0.1% | 1.1 | 1.0 | 2.1 | 2.1 | 1.0 | | | | | |
| NUMBER OF GENES | 0 | 0 | 1 | 1 | 0 | 5 | 4 | 5 | Non-sensitizing | |
| Hydroquinone | | | | | | | | | | |
| hydroquinone-50% | 1.7 | 2.0 | 5.4 | 3.8 | 0.9 | | | | | |
| NUMBER OF GENES | 1 | 1 | 1 | 1 | 0 | 15 | 11 | 15 | Sensitizing | STRONG |
| hydroquinone-10% | 1.3 | 1.5 | 1.6 | 2.0 | 0.6 | | | | | |
| NUMBER OF GENES | 0 | 1 | 1 | 1 | 0 | 13 | 4 | 13 | Sensitizing | |
| hydroquinone-1% | 1.5 | 1.4 | 1.5 | 1.8 | 0.6 | | | | | |
| NUMBER OF GENES | 1 | 1 | 1 | 1 | 0 | 9 | 5 | 9 | Sensitizing | |
| hydroquinone-0.1% | 0.8 | 0.9 | 1.3 | 0.7 | 0.8 | | | | | |
| NUMBER OF GENES | 0 | 0 | 0 | 0 | 0 | 5 | 2 | 5 | Non-sensitizing | |

|  | DAPK2 | CTSS | EHF | NGAL | S100A8 | DEFB1 | P13 | CXCR1 | IL1R2 | FABP4 | IVL | CD36 | HSP27 |
|---|---|---|---|---|---|---|---|---|---|---|---|---|---|
| Isoeugenol | | | | | | | | | | | | | |
| isoeugenol-50% | 1.4 | 1.4 | 2.0 | 2.7 | 1.5 | 2.1 | 1.7 | 2.6 | 1.7 | 1.8 | 2.8 | 0.6 | 1.2 |
| NUMBER OF GENES | 1 | 1 | 1 | 1 | 1 | 1 | 1 | 1 | 1 | 1 | 1 | 0 | 0 |
| isoeugenol-10% | 0.9 | 1.5 | 1.4 | 2.1 | 1.3 | 1.5 | 1.4 | 1.6 | 1.4 | 1.2 | 1.9 | 0.6 | 0.9 |
| NUMBER OF GENES | 0 | 1 | 1 | 1 | 1 | 1 | 1 | 1 | 1 | 0 | 1 | 0 | 0 |
| isoeugenol-1% | 0.9 | 0.8 | 1.2 | 1.1 | 1.0 | 1.1 | 0.9 | 1.1 | 1.4 | 0.9 | 1.4 | 1.3 | 0.8 |
| NUMBER OF GENES | 0 | 0 | 0 | 0 | 0 | 0 | 0 | 0 | 1 | 0 | 1 | 1 | 0 |
| isoeugenol-0.1% | 1.1 | 0.9 | 1.5 | 1.1 | 1.1 | 1.0 | 1.1 | 0.7 | 1.2 | 0.8 | 1.3 | 0.9 | 1.0 |
| NUMBER OF GENES | 0 | 0 | 1 | 0 | 0 | 0 | 0 | 0 | 0 | 0 | 1 | 0 | 0 |
| Glyoxal | | | | | | | | | | | | | |
| Glyoxal-50% | 0.9 | 2.7 | 0.9 | 0.6 | 0.9 | 1.6 | 1.4 | 2.7 | 2.0 | 0.8 | 1.5 | 1.1 | 0.8 |
| NUMBER OF GENES | 0 | 1 | 0 | 0 | 0 | 1 | 1 | 1 | 1 | 0 | 1 | 0 | 0 |

-continued

| | | | | | | | | | | | | |
|---|---|---|---|---|---|---|---|---|---|---|---|---|
| Glyoxal-10% | 0.9 | 2.2 | 0.9 | 1.3 | 0.9 | 1.6 | 1.3 | 1.8 | 2.2 | 0.8 | 1.6 | 1.3 | 0.8 |
| NUMBER OF GENES | 0 | 1 | 0 | 1 | 0 | 1 | 1 | 1 | 1 | 0 | 1 | 1 | 0 |
| Glyoxal-1% | 0.9 | 1.3 | 0.9 | 0.6 | 0.9 | 1.4 | 1.4 | 1.6 | 1.4 | 0.8 | 1.7 | 1.1 | 0.8 |
| NUMBER OF GENES | 0 | 1 | 0 | 0 | 0 | 1 | 1 | 1 | 1 | 0 | 1 | 0 | 0 |
| Glyoxal-0.1% | 0.9 | 1.0 | 0.8 | 0.7 | 0.7 | 0.8 | 0.8 | 1.1 | 0.9 | 0.4 | 0.7 | 1.1 | 0.7 |
| NUMBER OF GENES | 0 | 0 | 0 | 0 | 0 | 0 | 0 | 0 | 0 | 0 | 0 | 0 | 0 |

| | KRT4 | BRAK | SERPINB3 | MELANA | HSP90 | PDZK1iP1 | IL18 | DHFR | TOTAL SENS | GCLC | NQO1 |
|---|---|---|---|---|---|---|---|---|---|---|---|
| Isoeugenol | | | | | | | | | | | |
| isoeugenol-50% | 1.2 | 0.6 | 1.5 | 0.4 | 1.7 | 1.1 | 0.8 | 0.9 | | 1.3 | 1.8 |
| NUMBER OF GENES | 0 | 0 | 1 | 0 | 1 | 0 | 0 | 0 | 13 | 1 | 1 |
| isoeugenol-10% | 1.0 | 0.8 | 1.1 | 0.6 | 1.3 | 1.0 | 0.7 | 0.9 | | 0.8 | 1.0 |
| NUMBER OF GENES | 0 | 0 | 0 | 0 | 1 | 0 | 0 | 0 | 10 | 0 | 0 |
| isoeugenol-1% | 0.8 | 0.9 | 1.2 | 1.4 | 1.3 | 1.1 | 1.1 | 0.9 | | 0.9 | 1.0 |
| NUMBER OF GENES | 0 | 0 | 0 | 1 | 1 | 0 | 0 | 0 | 5 | 0 | 0 |
| isoeugenol-0.1% | 1.2 | 0.6 | 1.2 | 0.9 | 0.9 | 1.0 | 0.6 | 0.8 | | 0.8 | 1.1 |
| NUMBER OF GENES | 0 | 0 | 0 | 0 | 0 | 0 | 0 | 0 | 2 | 0 | 0 |
| Glyoxal | | | | | | | | | | | |
| Glyoxal-50% | 0.6 | 0.5 | 1.7 | 1.1 | 2.0 | 1.0 | 1.0 | 0.9 | | 0.9 | 0.9 |
| NUMBER OF GENES | 0 | 0 | 1 | 0 | 1 | 0 | 0 | 0 | 8 | 0 | 0 |
| Glyoxal-10% | 1.4 | 0.5 | 1.3 | 1.1 | 1.5 | 1.4 | 1.3 | 0.9 | | 1.1 | 1.2 |
| NUMBER OF GENES | 1 | 0 | 1 | 0 | 1 | 1 | 1 | 0 | 13 | 0 | 0 |
| Glyoxal-1% | 0.6 | 0.5 | 1.1 | 1.1 | 1.1 | 1.0 | 1.0 | 0.9 | | 1.1 | 1.1 |
| NUMBER OF GENES | 0 | 0 | 0 | 0 | 0 | 0 | 0 | 0 | 6 | 0 | 0 |
| Glyoxal-0.1% | 0.9 | 0.6 | 1.0 | 0.5 | 1.0 | 0.9 | 0.8 | 0.9 | | 1.0 | 1.0 |
| NUMBER OF GENES | 0 | 0 | 0 | 0 | 0 | 0 | 0 | 0 | 0 | 0 | 0 |

| | FTL | FTH1P | AKR1B10 | AKR1C2 | AKR1C1 | CYP1B1 | CYP1A1 | TXNRD1 | HMOX1 | UGT1A1 |
|---|---|---|---|---|---|---|---|---|---|---|
| Isoeugenol | | | | | | | | | | |
| isoeugenol-50% | 1.5 | 1.0 | 1.0 | 1.3 | 2.2 | 39.1 | 87.1 | 2.6 | 1.4 | 1.2 |
| NUMBER OF GENES | 1 | 0 | 0 | 1 | 1 | 1 | 1 | 1 | 1 | 0 |
| isoeugenol-10% | 0.9 | 0.9 | 0.5 | 0.7 | 1.1 | 39.8 | 510.5 | 1.5 | 1.2 | 1.2 |
| NUMBER OF GENES | 0 | 0 | 0 | 0 | 0 | 1 | 1 | 1 | 0 | 0 |
| isoeugenol-1% | 1.0 | 0.9 | 0.7 | 0.9 | 1.2 | 25.3 | 219.2 | 1.3 | 1.2 | 1.1 |
| NUMBER OF GENES | 0 | 0 | 0 | 0 | 0 | 1 | 1 | 1 | 0 | 0 |
| isoeugenol-0.1% | 1.0 | 0.8 | 0.9 | 1.0 | 1.1 | 12.2 | 11.9 | 1.1 | 0.9 | 1.0 |
| NUMBER OF GENES | 0 | 0 | 0 | 0 | 0 | 1 | 1 | 0 | 0 | 0 |
| Glyoxal | | | | | | | | | | |
| Glyoxal-50% | 0.9 | 0.9 | 0.8 | 0.9 | 0.8 | 3.3 | 1.1 | 1.4 | 1.4 | 1.4 |
| NUMBER OF GENES | 0 | 0 | 0 | 0 | 0 | 1 | 0 | 1 | 1 | 1 |
| Glyoxal-10% | 1.1 | 1.1 | 0.7 | 1.2 | 1.0 | 0.8 | 0.0 | 1.3 | 1.0 | 1.0 |
| NUMBER OF GENES | 0 | 0 | 0 | 0 | 0 | 0 | 0 | 1 | 0 | 0 |
| Glyoxal-1% | 1.1 | 1.0 | 1.1 | 1.0 | 1.0 | 1.1 | 0.9 | 0.9 | 0.9 | 1.2 |
| NUMBER OF GENES | 0 | 0 | 0 | 0 | 0 | 0 | 0 | 0 | 0 | 0 |
| Glyoxal-0.1% | 1.0 | 0.9 | 0.6 | 0.8 | 0.8 | 0.6 | 0.6 | 1.0 | 1.0 | 0.9 |
| NUMBER OF GENES | 0 | 0 | 0 | 0 | 0 | 0 | 0 | 0 | 0 | 0 |

| | UGT1A9 | NQO2 | SLC7A11 | GCLM | AHR | TOTAL ARE | SENS >1.3 | ARE >1.3 | | |
|---|---|---|---|---|---|---|---|---|---|---|
| Isoeugenol | | | | | | | | | | |
| isoeugenol-50% | 1.2 | 1.1 | 2.2 | 2.0 | 1.0 | | | | | |
| NUMBER OF GENES | 0 | 0 | 1 | 1 | 0 | 11 | 13 | 11 | Sensitizing | MODERATE |
| isoeugenol-10% | 1.6 | 0.9 | 1.1 | 1.5 | 0.9 | | | | | |

-continued

| | | | | | | | | | | |
|---|---|---|---|---|---|---|---|---|---|---|
| NUMBER OF GENES | 1 | 0 | 0 | 1 | 0 | 5 | 10 | 5 | Sensitizing | |
| isoeugenol-1% | 1.0 | 1.0 | 1.1 | 1.2 | 0.9 | | | | | |
| NUMBER OF GENES | 0 | 0 | 0 | 0 | 0 | 3 | 5 | 3 | Sensitizing | |
| isoeugenol-0.1% | 0.8 | 1.0 | 1.1 | 1.1 | 0.7 | | | | | |
| NUMBER OF GENES | 0 | 0 | 0 | 0 | 0 | 2 | 2 | 2 | Sensitizing | |
| Glyoxal | | | | | | | | | | |
| Glyoxal-50% | 1.3 | 0.9 | 1.0 | 1.5 | 0.9 | | | | | |
| NUMBER OF GENES | 1 | 0 | 0 | 1 | 0 | 6 | 8 | 6 | Sensitizing | MODERATE |
| Glyoxal-10% | 0.2 | 1.0 | 1.9 | 1.7 | 1.0 | | | | | |
| NUMBER OF GENES | 0 | 0 | 1 | 1 | 0 | 3 | 13 | 3 | Sensitizing | |
| Glyoxal-1% | 0.6 | 1.0 | 1.4 | 0.9 | 1.1 | | | | | |
| NUMBER OF GENES | 0 | 0 | 1 | 0 | 0 | 1 | 6 | 1 | Sensitizing | |
| Glyoxal-0.1% | 0.3 | 0.8 | 1.0 | 0.9 | 0.9 | | | | | |
| NUMBER OF GENES | 0 | 0 | 0 | 0 | 0 | 0 | 0 | 0 | Sensitizing | |

| | DAPK2 | CTSS | EHF | NGAL | S100A8 | DEFB1 | P13 | CXCR1 | IL1R2 | FABP4 | IVL | CD36 | HSP27 |
|---|---|---|---|---|---|---|---|---|---|---|---|---|---|
| Eugenol | | | | | | | | | | | | | |
| Eugenol-50% | 1.5 | 0.1 | 1.2 | 1.3 | 1.9 | 3.0 | 1.4 | 2.2 | 1.3 | 1.4 | 2.6 | 2.3 | 5.4 |
| NUMBER OF GENES | 1 | 0 | 0 | 1 | 1 | 1 | 1 | 1 | 1 | 1 | 1 | 1 | 1 |
| Eugenol-10% | 1.3 | 1.0 | 1.3 | 0.7 | 1.0 | 1.1 | 0.9 | 0.8 | 0.8 | 0.6 | 0.9 | 1.7 | 1.1 |
| NUMBER OF GENES | 1 | 0 | 1 | 0 | 0 | 0 | 0 | 0 | 0 | 0 | 0 | 1 | 0 |
| alpha hexyl cinnamaldehyde | | | | | | | | | | | | | |
| HCA-50% | 0.8 | 0.8 | 1.3 | 1.1 | 1.1 | 1.1 | 1.0 | 1.2 | 1.1 | 1.2 | 1.4 | 1.9 | 1.1 |
| NUMBER OF GENES | 0 | 0 | 1 | 0 | 0 | 0 | 0 | 0 | 0 | 0 | 1 | 1 | 0 |
| HCA-10% | 1.0 | 1.0 | 1.0 | 0.8 | 1.0 | 0.9 | 0.9 | 0.7 | 0.8 | 0.8 | 0.9 | 2.2 | 1.0 |
| NUMBER OF GENES | 0 | 0 | 0 | 0 | 0 | 0 | 0 | 0 | 0 | 0 | 0 | 0 | 0 |
| ipropylene glycol | | | | | | | | | | | | | |
| DPG-50% | 1.3 | 1.2 | 0.9 | 1.0 | 1.2 | 1.2 | 1.0 | 2.2 | 1.2 | 1.2 | 1.1 | 1.1 | 1.1 |
| NUMBER OF GENES | 1 | 0 | 0 | 0 | 0 | 0 | 0 | 1 | 0 | 0 | 0 | 0 | 0 |
| DPG-10% | 1.4 | 0.7 | 1.0 | 0.6 | 1.1 | 0.9 | 1.0 | 0.5 | 1.0 | 0.8 | 0.9 | 1.1 | 1.2 |

| | KRT4 | BRAK | SERPINB3 | MELANA | HSP90 | PDZK1iP1 | IL18 | DHFR | TOTAL SENS |
|---|---|---|---|---|---|---|---|---|---|
| Eugenol | | | | | | | | | |
| Eugenol-50% | 4.6 | 0.4 | 1.4 | 1.0 | 9.1 | 1.7 | 0.7 | 0.6 | |
| NUMBER OF GENES | 1 | 0 | 1 | 0 | 1 | 1 | 0 | 0 | 15 |
| Eugenol-10% | 0.8 | 0.7 | 1.2 | 1.9 | 1.1 | 0.9 | 1.1 | 0.8 | |
| NUMBER OF GENES | 0 | 0 | 0 | 1 | 0 | 0 | 0 | 0 | 4 |
| alpha hexyl cinnamaldehyde | | | | | | | | | |
| HCA-50% | 1.0 | 0.8 | 1.2 | 1.3 | 1.7 | 1.1 | 1.0 | 0.9 | |
| NUMBER OF GENES | 0 | 0 | 0 | 1 | 1 | 0 | 0 | 0 | 5 |
| HCA-10% | 0.7 | 1.0 | 1.5 | 2.0 | 1.6 | 1.1 | 1.1 | 0.8 | |
| NUMBER OF GENES | 0 | 0 | 0 | 1 | 1 | 0 | 0 | 0 | 2 |
| ipropylene glycol | | | | | | | | | |
| DPG-50% | 1.3 | 1.1 | 1.1 | 0.6 | 1.0 | 1.1 | 1.2 | 1.2 | |
| NUMBER OF GENES | 1 | 0 | 0 | 0 | 0 | 0 | 0 | 0 | 3 |
| DPG-10% | 1.1 | 0.8 | 1.2 | 0.6 | 0.9 | 1.0 | 1.1 | 1.1 | |

| | GCLC | NQO1 | FTL | FTH1P | AKR1B10 | AKR1C2 | AKR1C1 | CYP1B1 | CYP1A1 | TXNRD1 | HMOX1 |
|---|---|---|---|---|---|---|---|---|---|---|---|
| Eugenol | | | | | | | | | | | |
| Eugenol-50% | 3.2 | 0.7 | 4.2 | 2.3 | 1.0 | 0.7 | 0.7 | 0.9 | 2.3 | 3.0 | 2.4 |
| NBRE GENES | 1 | 1 | 0 | 1 | 1 | 0 | 0 | 0 | 0 | 1 | 1 |
| Eugenol-10% | 1.3 | 1.1 | 1.1 | 1.1 | 0.9 | 1.1 | 1.3 | 0.6 | 0.5 | 1.1 | 1.3 |
| NBRE GENES | 1 | 0 | 0 | 0 | 0 | 0 | 1 | 0 | 0 | 0 | 1 |
| alpha hexyl | | | | | | | | | | | |

-continued

| cinnamaldehyde | | | | | | | | | | | |
|---|---|---|---|---|---|---|---|---|---|---|---|
| HCA-50% | 0.9 | 1.5 | 1.7 | 1.0 | 1.1 | 1.2 | 1.1 | 1.7 | 12.3 | 1.5 | 1.0 |
| NBRE GENES | 0 | 1 | 1 | 0 | 0 | 1 | 0 | 1 | 1 | 1 | 0 |
| HCA-10% | 1.0 | 1.2 | 1.1 | 1.1 | 1.1 | 1.1 | 0.9 | 0.8 | 0.3 | 0.9 | 1.1 |
| NBRE GENES | 0 | 0 | 0 | 0 | 0 | 0 | 0 | 0 | 0 | 0 | 0 |
| Dipropylene glycol | | | | | | | | | | | |
| DPG-50% | 1.0 | 1.2 | 1.2 | 1.2 | 1.1 | 1.4 | 1.2 | 1.6 | 1.5 | 1.2 | 1.1 |
| NBRE GENES | 0 | 0 | 0 | 0 | 0 | 1 | 0 | 1 | 1 | 0 | 0 |
| DPG-10% | 1.1 | 1.0 | 1.0 | 1.1 | 1.0 | 0.9 | 1.3 | 0.4 | 0.2 | 1.1 | 1.1 |
| NBRE GENES | 0 | 0 | 0 | 0 | 0 | 1 | 0 | 0 | 0 | 0 | 0 |

| | UGT1A1 | UGT1A9 | NQO2 | SLC7A11 | GCLM | AHR | TOTAL ARE | SENS >1.3 | ARE >1.3 | | |
|---|---|---|---|---|---|---|---|---|---|---|---|
| Eugenol | | | | | | | | | | | |
| Eugenol-50% | 0.5 | 25.0 | 1.3 | 2.6 | 1.1 | 1.3 | | | | | |
| NBRE GENES | 1 | 1 | 1 | 1 | 0 | 1 | 10 | 15 | 10 | Sensitizing | WEAK |
| Eugenol-10% | 1.0 | 0.7 | 1.0 | 1.2 | 1.1 | 0.8 | | | | | |
| NBRE GENES | 1 | 0 | 0 | 0 | 0 | 0 | 3 | 4 | 3 | Non-sensitizing | |
| alpha hexyl cinnamaldehyde | | | | | | | | | | | |
| HCA-50% | 0.8 | 1.6 | 1.2 | 1.3 | 1.2 | 1.0 | | | | | |
| NBRE GENES | 0 | 1 | 0 | 1 | 0 | 0 | 8 | 5 | 8 | Sensitizing | WEAK |
| HCA-10% | 0.7 | 0.7 | 1.1 | 0.8 | 0.8 | 0.8 | | | | | |
| NBRE GENES | 0 | 0 | 0 | 0 | 0 | 0 | 0 | 2 | 0 | Non-sensitizing | |
| Dipropylene glycol | | | | | | | | | | | |
| DPG-50% | 1.3 | 1.2 | 1.3 | 0.9 | 1.0 | 0.9 | | | | | |
| NBRE GENES | 0 | 0 | 1 | 0 | 0 | 0 | 4 | 3 | 4 | Non-sensitizing | |
| DPG-10% | 1.2 | 0.4 | 1.0 | 1.1 | 1.0 | 0.9 | | | | | |
| NBRE GENES | 0 | 0 | 0 | 0 | 0 | 0 | 1 | 1 | 1 | | |

| | DAPK2 | CTSS | EHF | NGAL | S100A8 | DEFB1 | P13 | CXCR1 | IL1R2 | FABP4 | IVL | CD36 | HSP27 |
|---|---|---|---|---|---|---|---|---|---|---|---|---|---|
| Acide Lactique | | | | | | | | | | | | | |
| Lactic acid 50% | 1.1 | 1.4 | 0.9 | 1.0 | 1.1 | 1.1 | 0.9 | 0.8 | 0.8 | 0.8 | 0.9 | 0.9 | 0.8 |
| NUMBER OF GENES | 0 | 1 | 0 | 0 | 0 | 0 | 0 | 0 | 0 | 0 | 0 | 0 | 0 |
| Lactic acid 10% | 1.1 | 1.1 | 0.9 | 1.0 | 1.0 | 1.0 | 0.8 | 0.7 | 1.0 | 0.9 | 0.9 | 1.1 | 0.9 |
| NUMBER OF GENES | 0 | 0 | 0 | 0 | 0 | 0 | 0 | 0 | 0 | 0 | 0 | 0 | 0 |
| Lactic acid 1% | 1.2 | 1.0 | 0.9 | 0.9 | 0.8 | 0.9 | 0.8 | 0.7 | 1.0 | 0.7 | 1.0 | 1.1 | 1.0 |
| NUMBER OF GENES | 0 | 0 | 0 | 0 | 0 | 0 | 0 | 0 | 0 | 0 | 0 | 0 | 0 |
| SLS | | | | | | | | | | | | | |
| SLS-50% (Corrosive) | 0.0 | 0.0 | 0.0 | 0.0 | 0.0 | 0.0 | 0.0 | 0.0 | 0.0 | 0.0 | 0.0 | 0.0 | 0.0 |
| NUMBER OF GENES | 0 | 0 | 0 | 0 | 0 | 0 | 0 | 0 | 0 | 0 | 0 | 0 | 0 |
| SLS-10% | 1.2 | 1.4 | 0.4 | 0.9 | 1.2 | 0.8 | 0.4 | 1.0 | 0.8 | 1.1 | 1.0 | 1.1 | 0.3 |
| NUMBER OF GENES | 0 | 1 | 0 | 0 | 0 | 0 | 0 | 0 | 0 | 0 | 0 | 0 | 0 |
| SLS-1% | 0.9 | 1.4 | 1.2 | 1.1 | 0.9 | 1.1 | 1.1 | 0.6 | 0.7 | 1.2 | 1.1 | 0.6 | 1.1 |
| NUMBER OF GENES | 0 | 1 | 0 | 0 | 0 | 0 | 0 | 0 | 0 | 0 | 0 | 0 | 0 |

| | KRT4 | BRAK | SERPINB3 | MELANA | HSP90 | PDZK1iP1 | IL18 | DHFR | TOTAL SENS |
|---|---|---|---|---|---|---|---|---|---|
| Acide Lactique | | | | | | | | | |
| Lactic acid 50% | 0.8 | 0.7 | 1.2 | 0.6 | 0.9 | 1.0 | 0.8 | 0.9 | |
| NUMBER OF GENES | 0 | 0 | 0 | 0 | 0 | 0 | 0 | 0 | 1 |
| Lactic acid 10% | 0.8 | 1.0 | 1.1 | 0.8 | 0.9 | 1.0 | 1.0 | 1.0 | |
| NUMBER OF GENES | 0 | 0 | 0 | 0 | 0 | 0 | 0 | 0 | 0 |
| Lactic acid 1% | 0.9 | 0.8 | 0.9 | 0.7 | 1.0 | 1.0 | 0.9 | 0.9 | |
| NUMBER OF GENES | 0 | 0 | 0 | 0 | 0 | 0 | 0 | 0 | 0 |

-continued

SLS

| | | | | | | | | | |
|---|---|---|---|---|---|---|---|---|---|
| SLS-50% (Corrosive) | 0.0 | 0.0 | 0.0 | 0.0 | 0.0 | 0.0 | 0.0 | 0.0 | |
| NUMBER OF GENES | 0 | 0 | 0 | 0 | 0 | 0 | 0 | 0 | 0 |
| SLS-10% | 0.7 | 1.4 | 0.7 | 2.5 | 0.7 | 0.6 | 1.0 | 1.2 | |
| NUMBER OF GENES | 0 | 1 | 0 | 1 | 0 | 0 | 0 | 0 | 3 |
| SLS-1% | 1.1 | 1.3 | 1.1 | 1.6 | 0.6 | 0.7 | 0.5 | 0.8 | |
| NUMBER OF GENES | 0 | 0 | 0 | 1 | 0 | 0 | 0 | 0 | 2 |

| | GCLC | NQO1 | FTL | FTH1P | AKR1B10 | AKR1C2 | AKR1C1 | CYP1B1 | CYP1A1 | TXNRD1 | HMOX1 |
|---|---|---|---|---|---|---|---|---|---|---|---|
| Acide Lactique | | | | | | | | | | | |
| Ac Lactique-50% | 0.9 | 1.0 | 1.1 | 0.9 | 1.0 | 0.8 | 1.2 | 1.0 | 1.1 | 1.0 | 1.0 |
| NUMBER OF GENES | 0 | 0 | 0 | 0 | 0 | 0 | 0 | 0 | 0 | 0 | 0 |
| Ac Lactique-10% | 0.9 | 1.0 | 1.0 | 0.9 | 1.0 | 1.0 | 1.2 | 1.3 | 1.8 | 1.2 | 1.1 |
| NUMBER OF GENES | 0 | 0 | 0 | 0 | 0 | 0 | 0 | 0 | 1 | 0 | 0 |
| Ac Lactique-1% | 1.0 | 0.9 | 1.2 | 1.1 | 0.7 | 1.0 | 1.0 | 1.1 | 0.6 | 1.0 | 0.9 |
| NUMBER OF GENES | 0 | 0 | 0 | 0 | 0 | 0 | 0 | 0 | 0 | 0 | 0 |
| SLS | | | | | | | | | | | |
| SLS-50% (Corrosif) | 0.0 | 0.0 | 0.0 | 0.0 | 0.0 | 0.0 | 0.0 | 0.0 | 0.0 | 0.0 | 0.0 |
| NUMBER OF GENES | 0 | 0 | 0 | 0 | 0 | 0 | 0 | 0 | 0 | 0 | 0 |
| SLS-10% | 1.7 | 1.1 | 1.6 | 1.3 | 1.1 | 1.2 | 1.6 | 0.3 | 0.2 | 1.2 | 0.5 |
| NUMBER OF GENES | 1 | 0 | 1 | 0 | 0 | 0 | 1 | 0 | 0 | 0 | 0 |
| SLS-1% | 1.3 | 1.1 | 1.2 | 1.0 | 1.0 | 1.1 | 1.0 | 0.6 | 1.0 | 0.9 | 0.4 |
| NUMBER OF GENES | 0 | 0 | 0 | 0 | 0 | 0 | 0 | 0 | 0 | 0 | 0 |

| | UGT1A1 | UGT1A9 | NQO2 | SLC7A11 | GCLM | AHR | TOTAL ARE | SENS >1.3 | ARE >1.3 | |
|---|---|---|---|---|---|---|---|---|---|---|
| Acide Lactique | | | | | | | | | | |
| Ac Lactique-50% | 1.3 | 0.8 | 1.2 | 1.0 | 1.1 | 0.8 | | | | |
| NUMBER OF GENES | 0 | 0 | 0 | 0 | 0 | 0 | 0 | 1 | 0 | Non-sensitizing |
| Ac Lactique-10% | 1.3 | 0.7 | 1.1 | 1.2 | 1.0 | 0.5 | | | | |
| NUMBER OF GENES | 0 | 0 | 0 | 0 | 0 | 0 | 1 | 0 | 1 | |
| Ac Lactique-1% | 0.8 | 0.4 | 0.9 | 1.0 | 0.8 | 0.9 | | | | |
| NUMBER OF GENES | 0 | 0 | 0 | 0 | 0 | 0 | 0 | 0 | 0 | |
| SLS | | | | | | | | | | |
| SLS-50% (Corrosif) | 0.0 | 0.0 | 0.0 | 0.0 | 0.0 | 0.0 | | | | |
| NUMBER OF GENES | 0 | 0 | 0 | 0 | 0 | 0 | 0 | 0 | 0 | |
| SLS-10% | 1.0 | 1.4 | 1.0 | 5.2 | 1.0 | 1.4 | | | | |
| NUMBER OF GENES | 0 | 0 | 0 | 1 | 0 | 1 | 5 | 3 | 5 | Non-sensitizing |
| SLS-1% | 0.5 | 0.6 | 1.1 | 2.9 | 1.0 | 1.2 | | | | |
| NUMBER OF GENES | 0 | 0 | 0 | 1 | 0 | 0 | 1 | 2 | 1 | |

The invention claimed is:

1. A method for evaluating the sensitizing potential of a test compound, comprising the steps of:
   a) contacting a test compound with a biological sample, wherein the biological sample is a skin sample reconstructed in vitro, and said skin sample comprises no Langerhans cells;
   b) determining in the contacted skin sample the expression level of at least six genes chosen in the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1 IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A 11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/ tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQO1 (NAD(P)H dehydrogenase, quinone 1) and S100A8 (S 100 calcium binding protein A8),
   in which the expression level of each of said at least six genes is determined by measuring the expression level of the polypeptide encoded by said at least six genes or a fragment thereof, or by determining the expression level of the mRNA from said at least six genes or a fragment thereof; and
   c) comparing the expression level of each of said at least six genes with a reference value,
   wherein overexpression of the at least six genes indicates that the test compound has a sensitizing potential.

2. The evaluation method according to claim 1, comprising an additional step of amplifying the mRNA or cDNA of each of said six genes, the complementary sequence thereof or a fragment thereof.

3. The method according to claim 1, in which step b) comprises measuring the expression of at least 7 genes selected from the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B 10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQO1 (NAD(P)H dehydrogenase, quinone 1) and S100A8 (S100 calcium binding protein A8).

4. The method according to claim 1, in which step b) is performed between 2 and 24 hours after step a).

5. The method according to claim 4, in which step b) is performed between 4 and 18 hours after step a).

6. The method according to claim 4, in which step b) is performed between 5 and 7 hours after step a).

7. The method according to claim 4, in which step b) is performed 6 hours after step a).

8. A method for evaluating the sensitizing power of a test compound, comprising the following steps:
   1) obtaining at least one test compound dilution, and
   2) determining the sensitizing potential of said test compound at said at least one dilution by a method such as defined according to claim 1.

9. The method according to claim 1, in which step b) comprises measuring the expression of at least 8 genes selected from the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQO1 (NAD(P)H dehydrogenase, quinone 1) and S100A8 (S100 calcium binding protein A8).

10. The method according to claim 1, in which step b) comprises measuring the expression of at least 9 genes selected from the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB 1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B 10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQO1 (NAD(P)H dehydrogenase, quinone 1) and S100A8 (S100 calcium binding protein A8).

11. The method according to claim 1, in which step b) comprises measuring the expression of at least 10 genes selected from the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B 10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQO1 (NAD(P)H dehydrogenase, quinone 1) and S100A8 (S100 calcium binding protein A8).

12. The method according to claim 1, in which step b) comprises measuring the expression of at least 11 genes selected from the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB 1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B 10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQO1 (NAD(P)H dehydrogenase, quinone 1) and S100A8 (S100 calcium binding protein A8).

13. The method according to claim 1, in which step b) comprises measuring the expression of at least 12 genes selected from the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQO1 (NAD(P)H dehydrogenase, quinone 1) and S100A8 (S100 calcium binding protein A8).

14. The method according to claim 1, in which step b) comprises measuring the expression of at least 13 genes selected from the group consisting of: BRAK (CXC chemokine ligand 14), CTSS (cathepsin S), DAPK2 (death-associated protein kinase 2), FABP4 (fatty acid binding protein 4), HSP27 (heat shock 27 kDa protein), IL18 (IL-18), HSP90 (heat shock 90 kDa protein), IL1R2 (interleukin-1 receptor type II), TPSAB1 (tryptase alpha/beta 1), CXCR1 (interleukin 8 receptor, alpha), DEFB1 (defensin, beta 1), DHFR (dihydrofolate reductase), EHF (ets homologous factor), IVL (involucrin) KRT4 (keratin 4), MELANA (melan-A), NGAL (lipocalin 2), PDZK1IP1 (PDZK1 interacting protein interaction 1), PI3 (peptidase inhibitor 3), PSME2 (proteasome activator subunit 2), SERPINB3 (serpin peptidase inhibitor member 3), AKR1B10 (aldo-keto reductase family 1, member B10), AKR1C1 (aldo-keto reductase family 1, member C1), AKR1C2 (aldo-keto reductase family 1, member C2), CYP1B1 (cytochrome P450, family 1, subfamily B, polypeptide 1), FTH1P (ferritin, heavy polypeptide 1), FTL (ferritin, light polypeptide 1), G6PD (glucose-6-phosphate dehydrogenase), GCLM (glutamate-cysteine ligase modifier subunit), NQO2 (NAD(P)H dehydrogenase, quinone 2), SLC7A11 (solute carrier family 7, Member 11), TXNRD1 (thioredoxin reductase 1), UGT1A1 (UDP glucuronosyltransferase 1 family, polypeptide A1), UGT1A9 (UDP glucuronosyltransferase 1 family, polypeptide A9), YWHAZ (tyrosine 3-monooxygenase/tryptophan 5-monooxygenase activation protein, zeta polypeptide), CD36 (CD36 molecule), CYP1A1 (cytochrome P450, family 1, subfamily A, polypeptide 1), GCLC (glutamate-cysteine ligase, catalytic subunit), HMOX1 (heme oxygenase 1), NQO1 (NAD(P)H dehydrogenase, quinone 1) and S100A8 (S100 calcium binding protein A8).

* * * * *